(12) United States Patent
Biggadike et al.

(10) Patent No.: US 7,943,651 B2
(45) Date of Patent: *May 17, 2011

(54) COMPOUNDS

(75) Inventors: Keith Biggadike, Stevenage (GB); Anthony William James Cooper, Stevenage (GB); David House, Stevenage (GB); Iain McFarlane McLay, Stevenage (GB)

(73) Assignee: Glaxo Group Limited, Middlesex (GB)

( * ) Notice: Subject to any disclaimer, the term of this patent is extended or adjusted under 35 U.S.C. 154(b) by 20 days.

This patent is subject to a terminal disclaimer.

(21) Appl. No.: 11/736,606

(22) Filed: Apr. 18, 2007

(65) Prior Publication Data

US 2007/0265326 A1 Nov. 15, 2007

(30) Foreign Application Priority Data

| Apr. 20, 2006 | (GB) | 0607840.6 |
| Oct. 13, 2006 | (GB) | 0620382.2 |
| Apr. 3, 2007 | (GB) | 0706515.4 |
| Apr. 3, 2007 | (GB) | 0706516.2 |

(51) Int. Cl.
C07D 231/56 (2006.01)
A01N 43/56 (2006.01)

(52) U.S. Cl. .................. 514/403; 548/362.1

(58) Field of Classification Search .................. None
See application file for complete search history.

(56) References Cited

U.S. PATENT DOCUMENTS

| 4,837,235 | A | 6/1989 | Bernstein et al. |
| 6,124,334 | A | 9/2000 | Hutchinson |
| 6,245,804 | B1 | 6/2001 | Lehmann et al. |
| 6,323,199 | B1 | 11/2001 | Lehmann et al. |
| 6,344,454 | B1 | 2/2002 | Lehmann et al. |
| 6,548,534 | B2 | 4/2003 | Lehmann et al. |
| 6,897,224 | B2 | 5/2005 | Jaroch et al. |
| 2005/0131226 | A1 | 6/2005 | Rehwinkel et al. |
| 2005/0171109 | A1 | 8/2005 | Rehwinkel et al. |
| 2005/0209324 | A1 | 9/2005 | Rehwinkel et al. |
| 2005/0222154 | A1 | 10/2005 | Rehwinkel et al. |
| 2005/0234250 | A1 | 10/2005 | Lee |
| 2005/0272823 | A1 | 12/2005 | Rehwinkel et al. |

FOREIGN PATENT DOCUMENTS

| EP | 540009 B1 | 8/1995 |
| WO | 98/54159 A1 | 6/1998 |
| WO | 00/32584 A1 | 11/1998 |
| WO | 03/082280 A1 | 10/2003 |
| WO | 03/082787 A1 | 10/2003 |
| WO | 03/082827 A1 | 10/2003 |
| WO | 03/101932 A1 | 12/2003 |
| WO | 03/104195 A1 | 12/2003 |
| WO | 2005/040145 A1 | 5/2004 |
| WO | 2004/063163 A1 | 7/2004 |
| WO | 2005/003098 A1 | 1/2005 |
| WO | 2005/030213 A1 | 4/2005 |
| WO | 2005/034939 A1 | 4/2005 |
| WO | 2005/035518 A1 | 4/2005 |
| WO | 2005/037811 A1 | 4/2005 |
| WO | 2005/095401 A1 | 10/2005 |
| WO | 2006/108699 A1 | 10/2006 |

OTHER PUBLICATIONS

Chawla et al., "Challenges in Polymorphism of Pharmaceuticals", CRIPS vol. 5, No. 1, Jan.-Mar. 2004 (4 Pages).*
Newman et al., "Solid-state analysis of the active pharmaceutical ingredient in drug products", DDT vol. 8, No. 19, Oct. 2003, p. 898-905.*
Brittain et al. #2 "Effects of pharmaceutical processing on drug polymorphs and solvates" in Polymorphism in Pharmaceutical Solids, vol. 95, p. 331-361.*
Epress-Pharma-Online (http://www.expresspharmaonline.com/20031023/edit02.shtml).*
Hacks Chemical Dictionary, Fourth Edition, Julius Grant, 1972, p. 203.*
A. Ray et al; Anti-inflammation: direct physical association and functional antagonism between transcription factor NF-KB and the glucocorticoid receptor; Chest; 1995; 107 (3); 139; The American College of Chest Physicians.
H. Schacke et al; Mechanisms Involved in the Side Effects of Glucocorticoids; Pharmacology and Therapeutics; 2002; 96; 23-43; Elsevier.
H. Konig et al; Interference between pathway-specific transcription factors: glucocorticoids antagonize phorbol ester-induced AP-1 activity without altering AP-1 site occupation in vivo; The EMBO Journal; 1992; 11 (6); 2241-6.
P. Barnes et al; Anti-inflammatory actions of steroids: molecular mechanisms; TIPS Reviews; Dec. 1993; 14; 436-441; Elsevier.
A. Cato et al; Molecular Mechanisms of Anti-inflammatory Action of Glucocorticoids; BioEssays; 1998; 18 (5); 371-378.
R. Cumming et al; Use of Inhaled Corticosteroids and the Risk of Cataracts; The New England Journal of Medicine; Jul. 3, 1997; 337/1; 8-14.
C. Wong et al; Inhaled corticosteroid use and bone-mineral density in patients with asthma; The Lancet; Apr. 22, 2000; 355; 1399-1403.
D. B. Allen; Do intranasal corticosteroids affect childhood growth?; Allergy; 2000; 62; 15-18.

(Continued)

Primary Examiner — Sun Jae Y. Loewe
(74) Attorney, Agent, or Firm — Nora Stein-Fernandez; Theodore R. Furman

(57) ABSTRACT

The present invention provides compounds of formula (I):

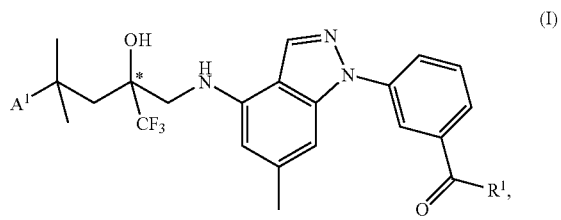

* = chiral centre pharmaceutical compositions comprising the compounds and the use of the compounds for the manufacture of a medicament, particularly for the treatment of inflammation and/or allergic conditions.

6 Claims, 2 Drawing Sheets

OTHER PUBLICATIONS

R. Pauwels et al; Long-Term Treatment with Inhaled Budesonide in Persons with Mild Chronic Obstructive Pulmonary Disease who Continue Smoking; The New England Journal of Medicine; Jun. 24, 1999; 340/25; 1948-1953.

J. Faul et al; High Dose Inhaled Corticosteroids and Dose Dependent Loss of Diabetic Control; BMJ; Nov. 28, 1998; 317; 1491.

S. Luo et al; Ytterbium Triflate Catalyzed Reactions of Epoxide with Nitrogen Heterocycles Under Solvent-Free Condition; Synthetic Communications; 2003; 33/17; 2989-2994; Marcel Dekker Inc.

R. Andrews et al; Glucocorticoids and insulin resistance: old hormones, new targets; Clinical Science; Apr. 16, 1999; 96; 513-523.

M. Massa et al; Novel Heteroaryl Replacements of Aromatic 3-Tetrafluoroethoxy Substituents in Trifluoro-3-(tertiaryamino)-2-propanols as Potent Inhibitors of Cholesteryl Ester Transfer Protein; Bioorganic & Medicinal Chemistry Letters; 2001; 11; 1625-1628; Pergamon.

T. Lee et al; A Concise Asymmetric Route for the Synthesis of a Novel Class of Glucocorticoid Mimetics Containing a Trifluoromethyl-Substituted Alcohol; Bioorganic & Medicinal Chemistry Letters; 2006; 16; 654-657; Elsevier.

J. Song et al; Practical Stereoselective Synthesis of an alpha-Trifluoromethyl-alpha-alkyl Epoxide via a Diastereoselective Trifluoromethylation Reaction; Journal of Organic Chemistry; 2007; 72; 292-294; American Chemical Society.

Q. Cai et al; Preparation of N-Aryl Compounds by Amino Acid-Promoted Ullmann-Type Coupling Reactions; Synthesis; 2005; 3; 496-499.

A. Klapars et al; A General and Efficient Copper Catalyst for the Amidation of Aryl Halides and the N-Arylation of Nitrogen Heterocycles; Journal of American Chemistry Society; 2001; 123; 7727-7729; American Chemcial Society.

J. Antilla et al; Copper-Diamine-Catalyzed N-Arylation of Pyrroles, Pyrazoles, Indazoles, Imidazoles, and Triazoles; Journal of Organic Chemistry; 2004; 69; 5578-5587; American Chemical Society.

A. Muci et al; Practical Palladium Catalysts for C-N and C-O Bond Formation; Topics of Current Chemistry; 2002; 219; 131-209; American Chemical Society.

M. Van Der Mey et al; Synthesis and Structure-Activity Relationships of cis-Tetrahydrophthalazinone/Pyridazinone Hybrids: A Novel Series of Potent Dual PDE3/PDE4 Inhibitory Agents; Journal of Medicinal Chemistry; 2003; 46; 2008-2016; American Chemical Society.

S. Lulinski et al; Regiospecific Metalation of Oligobromobenzenes; Journal of Organic Chemistry; 2003; 68; 5384-5387; American Chemical Society.

F. Harden et al; Synthesis and Adenosine Receptor Affinity of a Series of Pyrazolo{3,4-d]pyrimidine Analogues of 1-Methylisoguanosine; Journal of Medicinal Chemistry; 1991; 34; 2892-2898; American Chemical Society.

J. Blair et al; Effect of Ring Fluorination on the Pharmacology of Hallucinogenic Tryptamines; Journal of Medicinal Chemistry; 2000; 43; 4701-4710; American Chemical Society.

Express-Pharma-Online (http://www.expresspharmaonline.com/20031023/edit/edit02.shtml).

U.S. Appl. No. 12/226,372, filed Oct. 16, 2008.

* cited by examiner

COMPOUNDS

CROSS-REFERENCE TO RELATED APPLICATIONS

This application claims the benefit of GB Application No. 0607840.6, filed Apr. 20, 2006; GB Application No. 0620382.2, filed Oct. 13, 2006; GB Application No. 0706515.4, filed Apr. 3, 2007; and GB Application No. 0706516.2, filed Apr. 3, 2007.

BACKGROUND OF THE INVENTION

The present invention relates to non-steroidal compounds, pharmaceutical compositions comprising the compounds and the use of the compounds for the manufacture of a medicament, particularly for the treatment of inflammation and/or allergic conditions.

SUMMARY OF THE INVENTION

Nuclear receptors are a class of structurally related proteins involved in the regulation of gene expression. The steroid hormone receptors are a subset of this family whose natural ligands typically comprise endogenous steroids such as estradiol (estrogen receptor), progesterone (progesterone receptor) and cortisol (glucocorticoid receptor). Man-made ligands to these receptors play an important role in human health, in particular the use of glucocorticoid agonists to treat a wide range of inflammatory conditions.

Glucocorticoids exert their actions at the glucocorticoid receptor (GR) through at least two intracellular mechanisms, transactivation and transrepression (see: Schacke, H., Docke, W-D. & Asadullah, K. (2002) *Pharmacol and Therapeutics* 96:23-43; Ray, A., Siegel, M. D., Prefontaine, K. E. & Ray, P. (1995) *Chest* 107:139 S; and Konig, H., Ponta, H., Rahmsdorf, H. J. & Herrlich, P. (1992) *EMBO J.* 11:2241-2246). Transactivation involves direct binding of the glucocorticoid receptor to distinct deoxyribonucleic acid (DNA) glucocorticoid response elements (GREs) within gene promoters, usually but not always increasing the transcription of the downstream gene product. Recently, it has been shown that the GR can also regulate gene expression through an additional pathway (transrepression) in which the GR does not bind directly to DNA. This mechanism involves interaction of the GR with other transcription factors, in particular NFkB and AP1, leading to inhibition of their pro-transcriptional activity (Schacke, H., Docke, W-D. & Asadullah, K. (2002) *Pharmacol and Therapeutics* 96:23-43; and Ray, A., Siegel, M. D., Prefontaine, K. E. & Ray, P. (1995) *Chest* 107:139 S). Many of the genes involved in the inflammatory response are transcriptionally activated through the NFkB and AP1 pathways and therefore inhibition of this pathway by glucocorticoids may explain their anti-inflammatory effect (see: Barnes, P. J. & Adcock, I. (1993) *Trend Pharmacol Sci* 14:436-441; and Cato, A. C. & Wade, E. (1996) *Bioessays* 18: 371-378).

Despite the effectiveness of glucocorticoids in treating a wide range of conditions, a number of side-effects are associated with pathological increases in endogenous cortisol or the use of exogenous, and particularly systemically administered, glucocorticoids. These include reduction in bone mineral density (Wong, C. A., Walsh, L. J., Smith, C. J. P. et al. (2000) *Lancet* 355:1399-1403), slowing of growth (Allen, D. B. (2000) *Allergy* 55: suppl 62, 15-18), skin bruising (Pauwels, R. A., Lofdahl, C-G., Latinen, L. A. et al. (1999) *N Engl J Med* 340:1948-1953), development of cataracts (Cumming, R. G., Mitchell, P. & Leeder, S. R. (1997) *N Engl J Med* 337:8-14) and dysregulation of lipid and glucose metabolism (Faul, J. L., Tormey, W., Tormey, V. & Burke, C. (1998) *BMJ* 317:1491; and Andrews, R. C. & Walker, B. R. (1999) *Clin Sci* 96:513-523). The side-effects are serious enough often to limit the dose of glucocorticoid that can be used to treat the underlying pathology leading to reduced efficacy of treatment.

Current known glucocorticoids have proved useful in the treatment of inflammation, tissue rejection, auto-immunity, various malignancies, such as leukemias and lymphomas, Cushing's syndrome, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia and Little's syndrome.

Glucocorticoids are especially useful in disease states involving systemic inflammation such as inflammatory bowel disease, systemic lupus erythematosus, polyarteritis nodosa, Wegener's granulomatosis, giant cell arteritis, rheumatoid arthritis, osteoarthritis, seasonal rhinitis, allergic rhinitis, vasomotor rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis and cirrhosis. Glucocorticoids have also been used as immunostimulants and repressors and as wound healing and tissue repair agents.

Glucocorticoids have also found use in the treatment of diseases such as inflammatory scalp alopecia, panniculitis, psoriasis, discoid lupus erythemnatosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform and cutaneous T-cell lymphoma.

In one embodiment, the present invention provides compounds of formula (I):

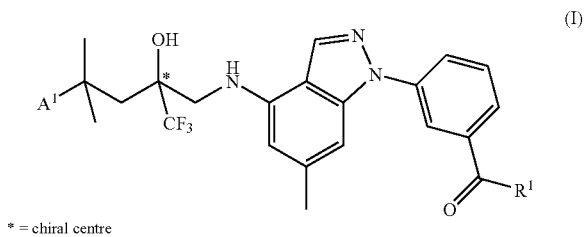

* = chiral centre wherein
$A^1$ represents 5-fluoro-2-methoxy-phenyl or 5-fluoro-2-hydroxy-phenyl;
$R^1$ represents —$N(R^2)C(R^3)(R^4)CONHR^5$ or

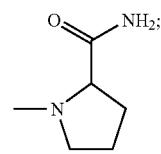

$R^2$ represents hydrogen or methyl;
$R^3$ represents hydrogen and $R^4$ represents hydrogen, methyl or hydroxymethyl, or $R^3$ and $R^4$ each represent methyl; and
$R^5$ represents hydrogen or methyl;
and physiologically functional derivatives thereof (hereinafter "compounds of the invention").

DETAILED DESCRIPTION OF THE INVENTION

In a further embodiment, the present invention provides compounds of formula (I):

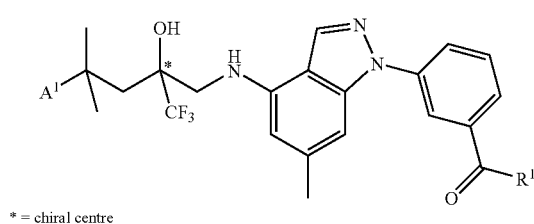

(I)

* = chiral centre wherein
$A^1$ represents 5-fluoro-2-methoxy-phenyl or 5-fluoro-2-hydroxy-phenyl;
$R^1$ represents —N($R^2$)C($R^3$)($R^4$)CONH$R^5$ or

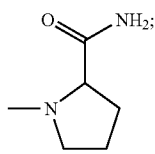

$R^2$ represents hydrogen or methyl;
$R^3$ represents hydrogen and $R^4$ represents hydrogen, methyl or hydroxymethyl, or $R^3$ and $R^4$ each represent methyl; and
$R^5$ represents hydrogen or methyl;
and physiologically functional derivatives thereof;
wherein the compound is not 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide or a physiologically functional derivative thereof.

Compounds of formula (I) contain one or two chiral centres. Thus there are up to four possible stereoisomers of each compound of formula (I). Further, at least one of the possible stereoisomers of each compound of formula (I) modulates the glucocorticoid receptor.

The term "modulator" is used herein to refer to a compound which may, for example, be an agonist, a partial agonist or antagonist of the glucocorticoid receptor. In one embodiment, a modulator of the glucocorticoid receptor may be an agonist of the glucocorticoid receptor.

Compounds of the invention may provide agonism of the glucocorticoid receptor.

Compounds of the invention may have suitable aqueous solubility to allow formulation as an aqueous solution, for example as an aqueous solution for intranasal administration.

It will be appreciated by those skilled in the art that at least one isomer (e.g. one enantiomer of a racemate) has the described activity. The other isomers may have similar activity, less activity, no activity or may have some antagonist activity in a functional assay.

The terms enantiomer A and enantiomer B are used herein to refer to the enantiomers of a compound of formula (I) based on the order of their elution using the chiral chromatography methodology described herein. Enantiomer A refers to the first enantiomer to elute, and enantiomer B refers to the second enantiomer to elute.

Similarly, the terms diastereomer A and diastereomer B are used herein to refer to the diastereomers of a compound of formula (I) based on their order of elution using the chiral chromatographic methodology described herein. Diastereomer A refers to the first diastereomer to elute, and diastereomer B refers to the second diastereomer to elute.

It will be appreciated by those skilled in the art that although the absolute retention time on chromatography can be variable, the order of elution remains the same when the same column and conditions are employed. However, the use of a different chromatography column and conditions may alter the order of elution.

A single enantiomer or diastereomer or mixture of isomers (e.g. racemic mixture) may be preferred. Thus in one embodiment of the invention, the compound of formula (I) is the enantiomer A. In a further embodiment of the invention, the compound of formula (I) is the diastereomer A.

Figure 1:
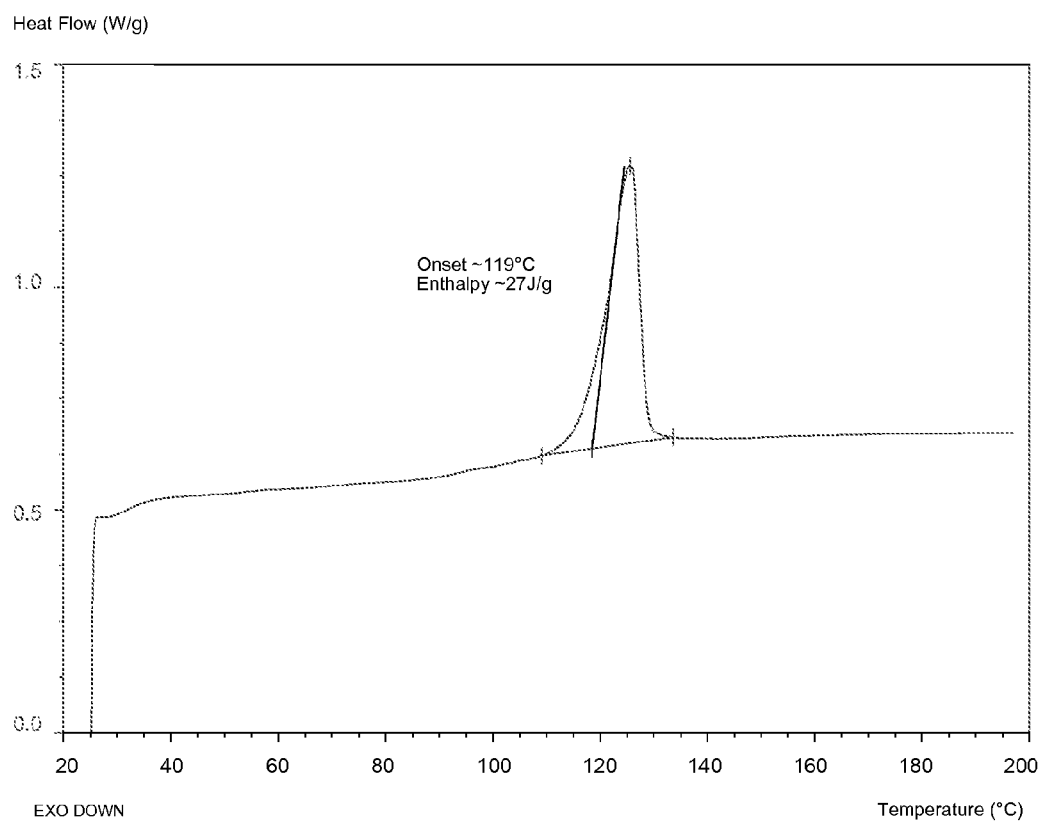
FIG. 1 illustrates a DSC thermogram for a crystalline form of 1-{[3-(4{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide.

In one embodiment, the invention provides compounds of formula (I) wherein $A^1$ represents 5-fluoro-2-methoxy-phenyl. In another embodiment, the invention provides compounds of formula (I) wherein $A^1$ represents 5-fluoro-2-hydroxy-phenyl.

In one embodiment, $R^1$ represents

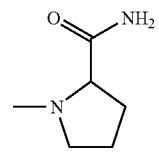

In a further embodiment, $R^1$ represents

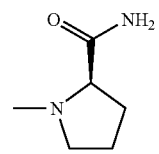

It is to be understood that the present invention encompasses all combinations of the substituent groups described above.

In one embodiment, the compound of formula (I) is:

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)benzamide;

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)benzamide (enantiomer A);

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)benzamide (enantiomer B);

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)-N-methylbenzamide;

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)-N-methylbenzamide (enantiomer A);

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)-N-methylbenzamide (enantiomer B);

N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide (diastereomer A);

N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide (diastereomer B);

N-[(1S)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-(2-amino-1,1-dimethyl-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-(2-amino-1,1-dimethyl-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide (enantiomer A);

N-(2-amino-1,1-dimethyl-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide (enantiomer B);

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-L-prolinamide;

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide;

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (diastereomer A);

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (diastereomer B);

N-[(1S)-2-amino-1-(hydroxymethyl)-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-(2-amino-2-oxoethyl)-3-(4-{[4-(5-fluoro-2-hydroxyphenyl)-2-hydroxy-4-methyl-2-(trifluoromethyl)pentyl] amino}-6-methyl-1H-indazol-1-yl)-N-methylbenzamide;

N-(2-amino-2-oxoethyl)-3-(4-{[4-(5-fluoro-2-hydroxyphenyl)-2-hydroxy-4-methyl-2-(trifluoromethyl)pentyl] amino}-6-methyl-1H-indazol-1-yl)benzamide;

N-[(1R)-2-amino-1-methyl-2-oxoethyl]-3-(4-{[4-(5-fluoro-2-hydroxyphenyl)-2-hydroxy-4-methyl-2-(trifluoromethyl)pentyl]amino}-6-methyl-1H-indazol-1-yl)benzamide;

1-{[3-(4-{[4-(5-fluoro-2-hydroxyphenyl)-2-hydroxy-4-methyl-2-(trifluoromethyl)pentyl]amino}-6-methyl-1H-indazol-1-yl)phenyl]carbonyl}-D-prolinamide;

3-(4-{[4-[5-fluoro-2-(methyloxy)phenyl]-2-hydroxy-4-methyl-2-(trifluoromethyl)pentyl]amino}-6-methyl-1H-indazol-1-yl)-N-[2-(methylamino)-2-oxoethyl]benzamide;

N-[(1S)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)-N-methylbenzamide;

N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)-N-methylbenzamide;

N-[(1R)-2-amino-1-(hydroxymethyl)-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

1-{[3-(4-{[(2R)-4-(5-fluoro-2-hydroxyphenyl)-2-hydroxy-4-methyl-2-(trifluoromethyl)pentyl]amino}-6-methyl-1H-indazol-1-yl)phenyl]carbonyl}-D-prolinamide; or a physiologically functional derivative thereof.

In another embodiment, the compound of formula (I) is:

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)benzamide;

N-(2-amino-2-oxoethyl)-3-(4-{[4-[5-fluoro-2-(methyloxy) phenyl]-2-hydroxy-4-methyl-2-(trifluoromethyl)pentyl] amino}-6-methyl-1H-indazol-1-yl)-N-methylbenzamide;

N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-[(1S)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-(2-amino-1,1-dimethyl-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-L-prolinamide;

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide;

N-[(1S)-2-amino-1-(hydroxymethyl)-2-oxoethyl]-3-(4-{[4-(5-fluoro-2-hydroxyphenyl)-2-hydroxy-4-methyl-2-(trifluoromethyl)pentyl]amino}-6-methyl-1H-indazol-1-yl) benzamide;

N-(2-amino-2-oxoethyl)-3-(4-{[4-(5-fluoro-2-hydroxyphenyl)-2-hydroxy-4-methyl-2-(trifluoromethyl)pentyl]amino}-6-methyl-1H-indazol-1-yl)-N-methylbenzamide;

N-(2-amino-2-oxoethyl)-3-(4-{[4-(5-fluoro-2-hydroxyphenyl)-2-hydroxy-4-methyl-2-(trifluoromethyl)pentyl]amino}-6-methyl-1H-indazol-1-yl)benzamide;

N-[(1R)-2-amino-1-methyl-2-oxoethyl]-3-(4-{[4-(5-fluoro-2-hydroxyphenyl)-2-hydroxy-4-methyl-2-(trifluoromethyl)pentyl]amino}-6-methyl-1H-indazol-1-yl)benzamide;

1-{[3-(4-{[4-(5-fluoro-2-hydroxyphenyl)-2-hydroxy-4-methyl-2-(trifluoromethyl)pentyl]amino}-6-methyl-1H-indazol-1-yl)phenyl]carbonyl}-D-prolinamide;

3-(4-{[4-[5-fluoro-2-(methyloxy)phenyl]-2-hydroxy-4-methyl-2-(trifluoromethyl)pentyl]amino}-6-methyl-1H-indazol-1-yl)-N-[2-(methylamino)-2-oxoethyl]benzamide;

N-[(1S)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)-N-methylbenzamide;

N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)-N-methylbenzamide;

N-[(1R)-2-amino-1-(hydroxymethyl)-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide; or a physiologically functional derivative thereof.

In another embodiment, the compound of formula (I) is:

N-(2-amino-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-(2-amino-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)-N-methylbenzamide;

N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-[(1S)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

N-(2-amino-1,1-dimethyl-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide;

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-L-prolinamide;

1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide;

N-[(1S)-2-amino-1-(hydroxymethyl)-2-oxoethyl]-3-(4-{[4-(5-fluoro-2-hydroxyphenyl)-2-hydroxy-4-methyl-2-(trifluoromethyl)pentyl]amino}-6-methyl-1H-indazol-1-yl)benzamide;

N-(2-amino-2-oxoethyl)-3-(4-{[4-(5-fluoro-2-hydroxyphenyl)-2-hydroxy-4-methyl-2-(trifluoromethyl)pentyl]amino}-6-methyl-1H-indazol-1-yl)-N-methylbenzamide;

N-(2-amino-2-oxoethyl)-3-(4-{[4-(5-fluoro-2-hydroxyphenyl)-2-hydroxy-4-methyl-2-(trifluoromethyl)pentyl]amino}-6-methyl-1H-indazol-1-yl)benzamide;

N-[(1R)-2-amino-1-methyl-2-oxoethyl]-3-(4-{[4-(5-fluoro-2-hydroxyphenyl)-2-hydroxy-4-methyl-2-(trifluoromethyl)pentyl]amino}-6-methyl-1H-indazol-1-yl)benzamide;

1-{[3-(4-{[4-(5-fluoro-2-hydroxyphenyl)-2-hydroxy-4-methyl-2-(trifluoromethyl)pentyl]amino}-6-methyl-1H-indazol-1-yl)phenyl]carbonyl}-D-prolinamide;

3-(4-{[4-[5-fluoro-2-(methyloxy)phenyl]-2-hydroxy-4-methyl-2-(trifluoromethyl)pentyl]amino}-6-methyl-1H-indazol-1-yl)-N-[2-(methylamino)-2-oxoethyl]benzamide;
or a physiologically functional derivative thereof.

In another embodiment, the compound of formula (I) is:

1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide;
or a physiologically functional derivative thereof.

In a further embodiment, the compound of formula (I) is:

1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide.

The invention includes physiologically functional derivatives of the compound of formula (I). By the term "physiologically functional derivative" is meant a chemical derivative of a compound of formula (I) having the same physiological function as a free compound of formula (I), for example, by being convertible in the body thereto and includes any pharmaceutically acceptable esters, carbonates, carbamates, salts and solvates of compounds of formula (I), and solvates of any pharmaceutically acceptable esters, carbonates, carbamates or salts of compounds of formula (I), which, upon administration to the recipient, are capable of providing (directly or indirectly) compounds of formula (I) or active metabolite or residue thereof. Thus one embodiment of the invention embraces compounds of formula (I) and pharmaceutically acceptable salts and solvates thereof. Another embodiment of the invention embraces compounds of formula (I) and pharmaceutically acceptable salts thereof. A further embodiment of the invention embraces compounds of formula (I).

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds of formula (I) and their pharmaceutically acceptable salts, solvates, and physiologically functional derivatives. Thus one embodiment of the invention embraces compounds of formula (I) and salts and solvates thereof. A further embodiment of the invention embraces compounds of formula (I) and salts thereof.

Suitable salts according to the invention include those formed with both organic and inorganic acids or bases. For example, suitable salts according to the invention are those formed with bases. Pharmaceutically acceptable acid addition salts may include those formed from strong acids, for example hydrochloric, hydrobromic and sulphuric acids, and strong sulphonic acids such as tosic, camphorsulphonic and methanesulphonic acids. Pharmaceutically acceptable base salts include alkali metal salts such as those of sodium and potassium.

Examples of solvates include hydrates.

The compounds of the invention may have the ability to crystallise in more than one form. This is a characteristic known as polymorphism, and it is understood that such polymorphic forms ("polymorphs") are within the scope of the present invention. Polymorphism generally can occur as a response to changes in temperature or pressure or both and can also result from variations in the crystallisation process. Polymorphs can be distinguished by various physical characteristics known in the art such as x-ray diffraction patterns, solubility, and melting point.

In one embodiment, the present invention provides 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide or a physiologically functional derivative thereof in crystalline form.

In another embodiment, the present invention provides 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide in crystalline form.

In another embodiment, the present invention provides crystalline 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide characterised in that it provides:
(i) a DSC (differential scanning calorimetry) thermogram having an endotherm with an onset temperature of about 112° C. to about 121° C., and/or
(ii) an XRPD (X-ray powder diffraction) pattern having peaks (°2θ) at about 5.7, about 7.1, about 8.2, about 10.0 and about 10.7.

In another embodiment, the present invention provides crystalline 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide characterised in that it provides a DSC thermogram substantially in accordance with FIG. 1.

In another embodiment, the present invention provides crystalline 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide characterised in that it provides an XRPD pattern comprising peaks substantially as set out in Table 2.

Figure 2:
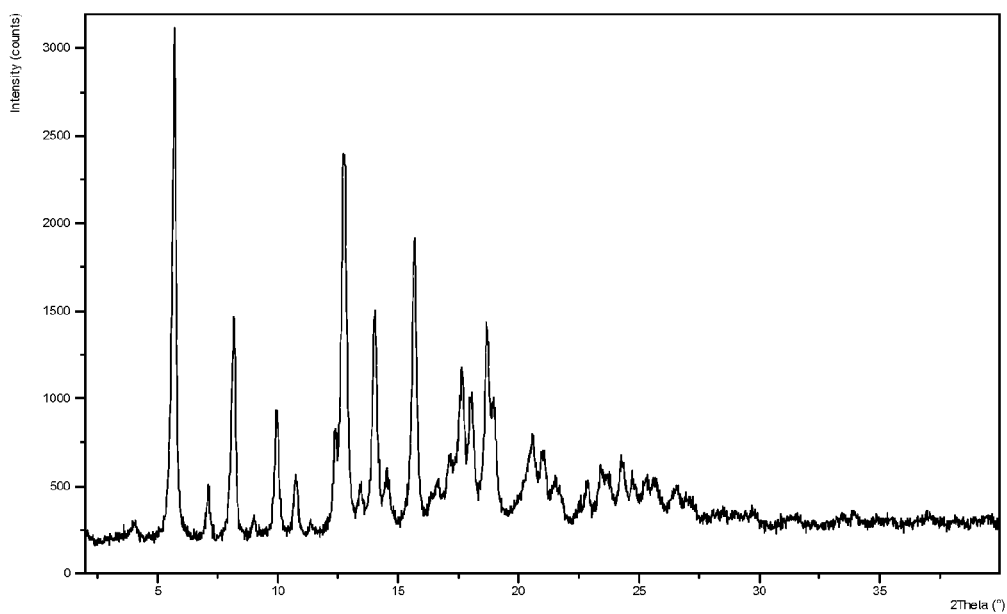
FIG. 2 illustrates an XRPD pattern of a crystalline form of 1-{[3-(4{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide.

In a further embodiment, the present invention provides crystalline 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide characterised in that it provides an XRPD pattern substantially in accordance with FIG. 2.

When it is indicated herein that there is an onset temperature at a given value, it is typically meant that the temperature is within ±1.5° C. of the value quoted.

When it is indicated herein that there is a peak in an XRPD pattern at a given value, it is typically meant that the peak is within ±0.2 of the value quoted.

The compounds of the invention are modulators of the glucocorticoid receptor and may be useful in the treatment of diseases associated with glucocorticoid receptor activity. Examples of diseases associated with glucocorticoid receptor activity include inflammation, tissue rejection, auto-immunity, various malignancies (such as leukemias and lymphomas), Cushing's syndrome, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, inflammatory scalp alopecia, panniculitis, psoriasis, discoid lupus erythemnatosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitus, erythema nodosum, acne, hirsutism, toxic epidermal necrolysis, erythema multiform and cutaneous T-cell lymphoma. Disease states involving systemic inflammation include inflammatory bowel disease, systemic lupus erythematosus, polyarteritis nodosa, Wegener's granulomatosis, giant cell arteritis, rheumatoid arthritis, osteoarthritis, seasonal rhinitis, allergic rhinitis, vasomotor rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis and cirrhosis. Glucocorticoid receptor modulators may also be used as immunostimulants and repressors and as wound healing and tissue repair agents.

The compounds of the invention are expected to have potentially beneficial anti-inflammatory and/or anti-allergic effects, particularly upon topical administration, demonstrated by, for example, their ability to bind to the glucocorticoid receptor and to illicit a response via that receptor. Hence, the compounds of the invention may be of use in the treatment of inflammatory and/or allergic disorders.

Examples of inflammatory and/or allergic disease states in which the compounds of the invention are expected to have utility include skin diseases such as eczema, psoriasis, allergic dermatitis, neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease (COPD), interstitial lung disease, and fibrosis; inflammatory bowel conditions such as ulcerative colitis and Crohn's disease; and auto-immune diseases such as rheumatoid arthritis.

The term "rhinitis" is used herein to refer to all types of rhinitis including allergic rhinitis such as seasonal rhinitis (for example hayfever) or perennial rhinitis, and non-allergic rhinitis or vasomotor rhinitis.

It will be appreciated by those skilled in the art that reference herein to treatment extends to prophylaxis as well as the treatment of established conditions.

As mentioned above, compounds of the invention are expected to be of use in human or veterinary medicine, in particular as anti-inflammatory and/or anti-allergic agents.

There is thus provided as a further aspect of the invention a compound of the invention for use in human or veterinary medicine, particularly in the treatment of patients with inflammatory and/or allergic conditions, such as rheumatoid arthritis, asthma, COPD, allergy and/or rhinitis. In one embodiment, the present invention provides a compound of the invention for use in the treatment of rhinitis, for example allergic rhinitis.

Further provided is a compound of the invention for use in the treatment of patients with skin disease such as eczema, psoriasis, allergic dermatitis, neurodermatitis, pruritis and/or hypersensitivity reactions.

According to another aspect of the invention, there is provided the use of a compound of the invention for the manufacture of a medicament for the treatment of patients with inflammatory and/or allergic conditions, such as rheumatoid arthritis, asthma, COPD, allergy and/or rhinitis. In one embodiment, the present invention provides the use of a compound of the invention for the manufacture of a medicament for the treatment of patients with rhinitis, for example allergic rhinitis.

According to yet to another aspect of the invention, there is provided the use of a compound of the invention for the manufacture of a medicament for the treatment of patients with skin disease such as eczema, psoriasis, allergic dermatitis, neurodermatitis, pruritis and/or hypersensitivity reactions.

In a further or alternative aspect, there is provided a method for the treatment of a human or animal subject with an inflammatory and/or allergic condition such as rheumatoid arthritis, asthma, COPD, allergy and/or rhinitis, which method comprises administering to said human or animal subject an effective amount of a compound of the invention. In one embodiment, there is provided a method for the treatment of a human or animal subject with rhinitis, for example allergic rhinitis, which method comprises administering to said human or animal subject an effective amount of a compound of the invention.

In yet a further or alternative aspect, there is provided a method for the treatment of a human or animal subject with skin disease such as eczema, psoriasis, allergic dermatitis, neurodermatitis, pruritis and/or hypersensitivity reactions, which method comprises administering to said human or animal subject an effective amount of a compound of the invention.

The compounds of the invention may be formulated for administration in any convenient way, and the invention therefore also includes within its scope pharmaceutical compositions comprising a compound of the invention together, if desirable, in admixture with one or more physiologically acceptable diluents and/or carriers.

Further, there is provided a process for the preparation of such pharmaceutical compositions which comprises mixing the ingredients. A pharmaceutical composition comprising a compound of the invention may be prepared by, for example, admixture at ambient temperature and atmospheric pressure.

Pharmaceutical compositions comprising a compound of the invention may be suitable for topical administration (which includes epicutaneous, inhaled, intranasal or ocular administration), enteral administration (which includes oral or rectal administration) or parenteral administration (such as by injection or infusion). The compounds of the invention may, for example, be formulated for oral, buccal, sublingual, parenteral, local rectal administration or other local administration.

Pharmaceutical compositions may be in the form of, for example, solutions or suspensions (aqueous or non-aqueous), tablet, capsules, oral liquid preparations, powders, granules, lozenges, lotions, creams, ointments, gels, foams, reconstitutable powders or suppositories as required by the route of administration.

Generally, compositions containing a compound of the invention may contain from about 0.1 to about 99%, such as from about 10 to about 60%, by weight based on the total weight of the composition, of the compound of the invention, depending on the route of administration. The dose of the compound used in the treatment of the above-mentioned disorders will vary in the usual way with the seriousness of the disorders, the weight of the sufferer and other similar factors. However, as a general guide, suitable unit doses may be about 0.001 to about 100 mg, for example about 0.001 to about 1 mg, and such unit doses may be administered more than once a day, for example two or three times a day. Such therapy may extend for a number of weeks or months.

Local administration as used herein includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

The proportion of the active compound of the invention in the local compositions according to the invention depends on the precise type of composition to be prepared, and the route of administration, but will generally be within the range of from 0.001 to 10% by weight based on the total weight of the composition. Generally, for most types of preparations, the proportion used will be within the range of from 0.005 to 1%, for example from 0.01 to 1%, such as 0.01 to 0.5% by weight based on the total weight of the composition. However, in powders for inhalation or insufflation the proportion used will normally be within the range of from 0.1 to 5% by weight based on the total weight of the composition.

In one embodiment, pharmaceutical compositions comprising a compound of the invention may be suitable for topical administration, for example for intranasal or inhaled administration. Inhaled administration involves topical administration to the lung, such as by aerosol or dry powder composition.

Generally, compositions suitable for intranasal or inhaled administration may conveniently be formulated as aerosols, solutions, suspensions, drops, gels or dry powders, optionally with one or more physiologically acceptable diluents and/or carriers such as aqueous or non-aqueous vehicles, thickening agents, isotonicity adjusting agents, antioxidants and/or preservatives.

For compositions suitable for intranasal or inhaled administration, the compound of the invention may be in a particle-size-reduced form prepared by, for example, micronisation and milling. Generally, the size-reduced (eg micronised) compound can be defined by a $D_{50}$ value of about 0.5 to about 10 microns (for example as measured using laser diffraction).

In one embodiment, pharmaceutical compositions comprising a compound of the invention are suitable for intranasal administration. For example, the compounds of the invention may be formulated for intranasal use in man either as a solution composition or a suspension composition, for example as a solution composition such as an aqueous solution composition.

A suitable dosing regime for an intranasal composition may be for the patient to inhale slowly through the nose subsequent to the nasal cavity being cleared. During inhalation, the composition may be administered to one nostril while the other is manually compressed. This procedure may then be repeated for the other nostril. Generally, one or two sprays per nostril may be administered by the above procedure up to two or three times each day. In one embodiment, the intranasal compositions comprising a compound of the invention are suitable for once daily administration. Typically, each spray to the nostril may deliver from about 25 to about 100 µL of intranasal composition. Further, generally, each spray to the nostril may deliver from about 1 to about 100 µg, for example about 1 to about 50 µg, of the compound of the invention.

Intranasal compositions comprising a compound of the invention may permit the compound to be delivered to all areas of the nasal cavities (the target tissue) and further, may permit the compound to remain in contact with the target tissue for longer periods of time. Compositions comprising a compound of the invention, suitable for intranasal administration, may optionally contain one or more suspending agents, one or more preservatives, one or more wetting agents and/or one or more isotonicity adjusting agents as desired. Compositions suitable for intranasal administration may optionally further contain other excipients such as antioxidants (for example sodium metabisulphite), taste-masking agents (for example menthol) and sweetening agents (for example dextrose, glycerol, saccharin and/or sorbitol). Excipients that may be employed in intranasal compositions include, for example, xylitol, potassium sorbate, EDTA, sodium citrate, citric acid, polysorbate 80 and Avicel CL611.

The suspending agent, if included, will typically be present in the intranasal composition in an amount of between about 0.1 and 5%, such as between about 1.5 and 2.4%, by weight based on the total weight of the composition. Examples of suspending agents include Avicel, carboxymethylcellulose, veegum, tragacanth, bentonite, methylcellulose and polyethylene glycols, e.g. microcrystalline cellulose or carboxy methylcellulose sodium. Suspending agents may also be included in, for example, compositions suitable for inhaled, ocular and oral administration, as appropriate.

For stability purposes, intranasal compositions comprising a compound of the invention may be protected from microbial or fungal contamination and growth by inclusion of a preservative. Examples of pharmaceutically acceptable anti-microbial agents or preservatives may include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives may include sodium benzoate. In one embodiment, there is provided a pharmaceutical composition comprising a compound of the invention which is benzalkonium chloride-free. The preservative, if included, may be present in an amount of between about 0.001 and about 1%, such as about 0.015%, by weight based on the total weight of the composition. Preservatives may be included in composition suitable for other routes of administration as appropriate.

Compositions which contain a suspended medicament may include a pharmaceutically acceptable wetting agent which functions to wet the particles of the medicament to facilitate dispersion thereof in the aqueous phase of the composition. Typically, the amount of wetting agent used will not cause foaming of the dispersion during mixing. Examples of wetting agents include fatty alcohols, esters and ethers, such as polyoxyethylene (20) sorbitan monooleate (polysorbate 80). The wetting agent may be present in the composition in an amount of between about 0.001 and about 1%, for example between about 0.005% and about 1%, by weight based on the total weight of the composition. Wetting agents may be included in compositions suitable for other routes of administration, e.g. for inhaled or ocular administration, as appropriate.

An isotonicity adjusting agent may be included to achieve isotonicity with body fluids e.g. fluids of the nasal cavity, resulting in reduced levels of irritancy. Examples of isotonicity adjusting agents include sodium chloride, dextrose, xylitol and calcium chloride. An isotonicity agent may be included in the composition in an amount of between about 0.1 and 10%, such as about 4.5% by weight based on the total weight of the composition. Isotonicity adjusting agents may also be included in, for example, compositions suitable for inhaled, ocular, oral and parenteral forms of administration, as appropriate.

Further, intranasal compositions may be buffered by the addition of suitable buffering agents such as sodium citrate, citric acid, phosphates such as disodium phosphate (for example dodecahydrate, heptahydrate, dihydrate and anhydrous forms) or sodium phosphate and mixtures thereof. Buffering agents may also be included in compositions suitable for other routes of administration, as appropriate.

Compositions for administration topically to the nose for example, for the treatment of rhinitis, include pressurised aerosol compositions and aqueous compositions administered to the nose by pressurised pump. In one embodiment, the present invention encompasses compositions which are non-pressurised and adapted to be administered topically to the nasal cavity. Suitable compositions contain water as the diluent or carrier for this purpose. Aqueous compositions for administration to the lung or nose may be provided with conventional excipients such as buffering agents, tonicity modifying agents and the like. Aqueous compositions may also be administered to the nose by nebulisation.

The compounds of the invention may be formulated as a fluid composition for delivery from a fluid dispenser, for example a fluid dispenser having a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid compositions. The housing has at least one finger-operable side lever which is movable inwardly with respect to the housing to cam the container upwardly in the housing to cause the pump to compress and pump a metered dose of the composition out of a pump stem through a nasal nozzle of the housing. In one embodiment, the fluid dispenser is of the general type illustrated in FIGS. 30-40 of WO05/044354.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid or derivative e.g. as described in WO94/21229 and WO98/34596 and cosolvents e.g. ethanol.

There is thus provided as a further aspect of the invention a pharmaceutical aerosol composition comprising a compound of the invention and a fluorocarbon or hydrogen-containing chlorofluorocarbon as propellant, optionally in combination with a surfactant and/or a cosolvent.

According to another aspect of the invention, there is provided a pharmaceutical aerosol composition wherein the propellant is selected from 1,1,1,2-tetrafluoroethane, 1,1,1,2,3,3,3-heptafluoro-n-propane and mixtures thereof.

The compositions of the invention may be buffered by the addition of suitable buffering agents.

Aerosol compositions may be presented in single or multidose quantities in sterile form in a sealed container, which may take the form of a cartridge or refill for use with an atomising device or inhaler. Alternatively, the sealed container may be a unitary dispensing device such as a single dose nasal inhaler or an aerosol dispenser fitted with a metering valve (metered dose inhaler), which is intended for disposal once the contents of the container have been exhausted.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain from 20 µg to 10 mg of the compound of formula (I). Alternatively, the compound of the invention may be presented without excipients such as lactose.

Optionally, in particular for dry powder inhalable compositions, a composition suitable for inhaled administration may be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition may be administered by inhalation via a device such as the DISKUS™ device, marketed by GlaxoSmithKline. The DISKUS™ inhalation device is, for example, described in GB2242134A, and in such a device, at least one container for the composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the composition in powder form from the opened container.

Aerosol compositions are preferably arranged so that each metered dose or "puff" of aerosol contains from 20 µg to 10 mg, preferably from 20 µg to 2000 µg, more preferably from 20 µg to 500 µg of a compound of formula (I). Administration may be once daily or several times daily, for example 2, 3, 4 or 8 times, giving for example 1, 2 or 3 doses each time. The overall daily dose with an aerosol will be within the range from 100 µg to 10 mg, preferably from 200 µg to 2000 µg. The overall daily dose and the metered dose delivered by capsules and cartridges in an inhaler or insufflator will generally be double that delivered with aerosol compositions.

In the case of suspension aerosol compositions, the particle size of the particulate (e.g., micronised) drug should be such as to permit inhalation of substantially all the drug into the lungs upon administration of the aerosol composition and will thus be less than 100 microns, desirably less than 20 microns, and in particular in the range of from 1 to 10 microns, such as from 1 to 5 microns, more preferably from 2 to 3 microns.

The compositions of the invention may be prepared by dispersal or dissolution of the medicament and a compound of the invention in the selected propellant in an appropriate container, for example, with the aid of sonication or a high-shear mixer. The process is desirably carried out under controlled humidity conditions.

The chemical and physical stability and the pharmaceutical acceptability of the aerosol compositions according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol compositions according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol compositions to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a composition metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g., see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, most preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the composition per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol compositions a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol compositions, a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied composition is added to an open canister under conditions which are sufficiently cold to ensure the composition does not vaporise, and then a metering valve crimped onto the canister.

Typically, in batches prepared for pharmaceutical use, each filled canister is check-weighed, coded with a batch number and packed into a tray for storage before release testing.

Topical preparations may be administered by one or more applications per day to the affected area; over skin areas occlusive dressings may advantageously be used. Continuous or prolonged delivery may be achieved by an adhesive reservoir system.

Ointments, creams (for example an oil-in-water or water-in-oil composition such as an emulsion) and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents. Topical preparations may also optionally contain one or more solubilising agents and/or skin penetration-enhancing agents and/or surfactants and/or fragrances and/or preservatives and/or emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

In one embodiment, there is provided a pharmaceutical composition comprising a compound of the invention which is suitable for ocular administration. Such compositions may optionally contain one or more suspending agents, one or more preservatives, one or more wetting/lubricating agents and/or one or more isotonicity adjusting agents. Examples of ophthalmic wetting/lubricating agents may include cellulose derivatives, dextran 70, gelatine, liquid polyols, polyvinyl alcohol and povidone such as cellulose derivatives and polyols.

For internal administration the compounds according to the invention may, for example, be formulated in conventional manner for oral, nasal, parenteral or rectal administration. Compositions for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms may be preferred.

The compounds of the invention may in general be given by internal administration in cases wherein systemic glucocorticoid receptor agonist therapy is indicated.

Slow release or enteric coated compositions may be advantageous, particularly for the treatment of inflammatory bowel disorders.

Fluid unit dosage forms for parenteral administration may be prepared using a compound of the invention and a sterile vehicle which may be aqueous or oil based. The compound, depending on the vehicle and concentration used, may be either suspended or dissolved in the vehicle. In preparing solutions, the compound of the invention may be dissolved for injection and filter sterilised before filling into a suitable vial or ampoule and sealing. Optionally, adjuvants such as a local anaesthetic, preservatives and buffering agents may be dissolved in the vehicle. To enhance the stability, the composition may be frozen after filling into the vial and the water removed under vacuum. The lyophilised parenteral composition may be reconstituted with a suitable solvent just prior to administration. Parenteral suspensions may be prepared in substantially the same manner, except that the compound is suspended in the vehicle instead of being dissolved, and sterilisation cannot be accomplished by filtration. The compound may be sterilised by exposure to ethylene oxide before suspension in a sterile vehicle. A surfactant or wetting agent may be included in the composition to facilitate uniform distribution of the compound.

In some embodiments, the compounds of the invention may be formulated for oral administration. In other embodiments, the compounds of the invention may be formulated for inhaled administration. In further embodiments, the compounds of the invention may be formulated for intranasal administration.

The compounds and pharmaceutical compositions according to the invention may be used in combination with or include one or more other therapeutic agents, for example selected from anti-inflammatory agents, anticholinergic agents (particularly an $M_1/M_2/M_3$ receptor antagonist), β₂-adrenoreceptor agonists, antiinfective agents such as antibiotics or antivirals, or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent such as a corticosteroid or an NSAID, an anticholinergic agent, a β₂-adrenoreceptor agonist, an antiinfective agent such as an antibiotic or an antiviral, or an antihistamine. One embodiment of the invention encompasses combinations comprising a compound of the invention together with a β₂-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising of a compound of the invention together with a β₂-adrenoreceptor agonist.

Examples of β₂-adrenoreceptor agonists include salmeterol (e.g. as the racemate or a single enantiomer, such as the R-enantiomer), salbutamol (e.g. as the racemate or a single enantiomer such as the R-enantiomer), formoterol (e.g. as the racemate or a single diastereomer such as the R,R-diastereomer), salmefamol, fenoterol, carmoterol, etanterol, naminterol, clenbuterol, pirbuterol, flerobuterol, reproterol, bambuterol, indacaterol or terbutaline and salts thereof, for example the xinafoate (1-hydroxy-2-naphthalenecarboxylate) salt of salmeterol, the sulphate salt or free base of salbutamol or the fumarate salt of formoterol. In one embodiment, the β₂-adrenoreceptor agonists are long-acting β₂-adrenoreceptor agonists, for example compounds which provide effective bronchodilation for about 12 hours or longer.

Examples of β₂-adrenoreceptor agonists may include those described in WO02/066422A, WO02/070490, WO02/076933, WO03/024439, WO03/072539, WO 03/091204, WO04/016578, WO04/022547, WO04/037807, WO04/037773, WO04/037768, WO04/039762, WO04/039766, WO01/42193 and WO03/042160.

Examples of β₂-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]foramide,
N-2{2-[4-(3-phenyl-4-methoxyphenyl)aminophenyl]ethyl}-2-hydroxy-2-(8-hydroxy-2(1H)-quinolinon-5-yl)ethylamine, and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one, and salts thereof.

The β₂-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Examples of corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl) oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17α-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy include those covered in the following published patent applications and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398 and WO06/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722.

In one embodiment, the invention provides the use of the compounds the invention in combination with a phosphodiesterase 4 (PDE4) inhibitor, for example in the case of a composition adapted for inhalation. The PDE4-specific inhibitor may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Another compound is cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P 2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728, PCT/EP2003/014867 (WO2004/056823) and PCT/EP2004/005494 (WO2004/103998 e.g. Example 399 or 544 disclosed therein), WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (for example, CAS 28797-61-7), darifenacin (for example, CAS 133099-04-4, or CAS 133099-07-7 for the hydrobromide sold under the name Enablex), oxybutynin (for example, CAS 5633-20-5, sold under the name Ditropan), terodiline (for example, CAS 15793-40-5), tolterodine (for example, CAS 124937-51-5, or CAS 124937-52-6 for the tartrate, sold under the name Detrol), otilonium (for example, as the bromide, CAS 26095-59-0, sold under the name Spasmomen), trospium chloride (for example, CAS 10405-02-4) and solifenacin (for example, CAS 242478-37-1, or CAS 242478-38-2, or the succinate also known as YM-905 and sold under the name Vesicare).

Additional compounds are disclosed in WO 2005/037280, WO 2005/046586 and WO 2005/104745, incorporated herein by reference. The present combinations include, but are not limited to:

(3-endo)-3-(2,2-di-2-thienylethenyl)-8,8-dimethyl-8-azoniabicyclo[3.2.1]octane iodide;

(3-endo)-3-(2-cyano-2,2-diphenylethyl)-8,8-dimethyl-8-azoniabicyclo[3.2.1]octane bromide;

4-[hydroxy(diphenyl)methyl]-1-{2-[(phenylmethyl)oxy]ethyl}-1-azoniabicyclo[2.2.2]octane bromide; and (1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds of formula (XXI), which are disclosed in U.S. patent application 60/487,981:

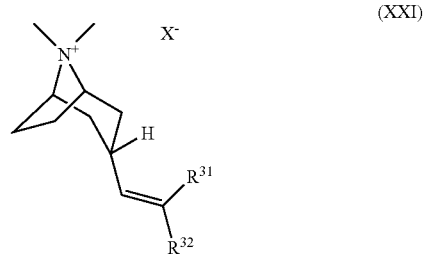

(XXI)

in which the preferred orientation of the alkyl chain attached to the tropane ring is endo; $R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds of formula (XXII) or (XXIII), which are disclosed in U.S. patent application 60/511,009:

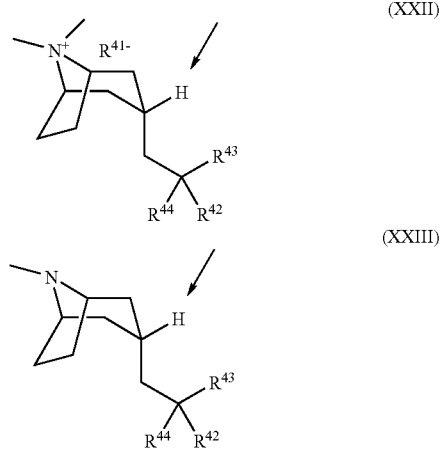

(XXII)

(XXIII)

wherein:
the H atom indicated is in the exo position;
$R^{41-}$ represents an anion associated with the positive charge of the N atom; $R^{41-}$ may be but is not limited to chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having from 6 to 10 carbon atoms), heterocycloalkyl (having from 5 to 6 carbon atoms) and N or O as the heteroatom, heterocycloalkyl-alkyl (having from 6 to 10 carbon atoms) and N or O as the heteroatom, aryl, optionally substituted aryl, heteroaryl, and optionally substituted heteroaryl;
$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —CN, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CO(R^{46})$—$CH_2N(R^{48})SO_2(R^{46})$—$CH_2N(R^{48})CO_2(R^{45})$, $CH_2N(R^{48})CONH(R^{47})$;
$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;
$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;
$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:

(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

Examples of antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, such as diphenylhydramine, pyrilamine, clemastine, chlorpheniramine. Second generation antagonists, which are non-sedating, include loratidine, desloratidine, terfenadine, astemizole, acrivastine, azelastine, levocetirizine fexofenadine and cetirizine.

Examples of anti-histamines include loratidine, desloratidine, fexofenadine, cetirizine, levocabastine, olopatadine, amlexanox and epinastine.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In another embodiment the invention provides a combination comprising a compound of formula (I), or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003). In a further embodiment, the invention provides a combination comprising a compound of formula (I) or a pharmaceutically acceptable salt thereof together with a dual H1/H3 antagonist. Examples of dual H1/H3 antagonists include 4-[(4-chlorophenyl)methyl]-2-({(2R)-1-[4-(4-{[3-(hexahydro-1H-azepin-1-yl)propyl]oxy}phenyl)butyl]-2-pyrrolidinyl}methyl)-1(2H)-phthalazinone or a pharmaceutically acceptable salt thereof as described in priority application GB0607839.8.

The invention thus provides, in a further aspect, a combination comprising a compound of formula (I) and/or a pharmaceutically acceptable salt, solvate or physiologically functional derivative thereof together with a PDE4 inhibitor.

The invention thus provides, in a further aspect, a combination comprising a compound of formula (I) and/or a pharmaceutically acceptable salt, solvate or physiologically functional derivative thereof together with a $\beta_2$-adrenoreceptor agonist.

The invention thus provides, in a further aspect, a combination comprising a compound of formula (I) and/or a pharmaceutically acceptable salt, solvate or physiologically functional derivative thereof together with a corticosteroid.

The invention thus provides, in a further aspect, a combination comprising a compound of formula (I) and/or a pharmaceutically acceptable salt, solvate or physiologically functional derivative thereof together with another non-steroidal GR agonist.

The invention thus provides, in a further aspect, a combination comprising a compound of formula (I) and/or a pharmaceutically acceptable salt, solvate or physiologically functional derivative thereof together with an anticholinergic.

The invention thus provides, in a further aspect, a combination comprising a compound of formula (I) and/or a pharmaceutically acceptable salt, solvate or physiologically functional derivative thereof together with an antihistamine.

The invention thus provides, in a further aspect, a combination comprising a compound of formula (I) and/or a pharmaceutically acceptable salt, solvate or physiologically functional derivative thereof together with a PDE4 inhibitor and a $\beta_2$-adrenoreceptor agonist.

The invention thus provides, in a further aspect, a combination comprising a compound of formula (I) and/or a pharmaceutically acceptable salt, solvate or physiologically functional derivative thereof together with an anticholinergic and a PDE-4 inhibitor.

The individual compounds of such combinations may be administered either sequentially or simultaneously in separate or combined pharmaceutical compositions. In one embodiment, the individual compounds will be administered simultaneously in a combined pharmaceutical composition. Appropriate doses of known therapeutic agents will readily be appreciated by those skilled in the art.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The invention thus provides, in a further aspect, a pharmaceutical composition comprising a combination of a compound of the invention together with another therapeutically active agent.

The invention thus provides, in a further aspect, a pharmaceutical composition comprising a combination of a compound of the invention together with a PDE4 inhibitor.

The invention thus provides, in a further aspect, a pharmaceutical composition comprising a combination of a compound of the invention together with a $\beta_2$-adrenoreceptor agonist.

The invention thus provides, in a further aspect, a pharmaceutical composition comprising a combination of a compound of the invention together with a corticosteroid.

The invention thus provides, in a further aspect, a pharmaceutical composition comprising a combination of a compound of the invention together with another non-steroidal GR agonist.

The invention thus provides, in a further aspect, a pharmaceutical composition comprising a combination of a compound of the invention together with an anticholinergic.

The invention thus provides, in a further aspect, a pharmaceutical composition comprising a combination of a compound of the invention together with an antihistamine.

The invention thus provides, in a further aspect, a pharmaceutical composition comprising a combination of a compound of the invention together with a PDE4 inhibitor and a $\beta_2$-adrenoreceptor agonist.

The invention thus provides, in a further aspect, a pharmaceutical composition comprising a combination of a compound of the invention together with an anticholinergic and a PDE-4 inhibitor.

A process according to the invention for the preparation of compounds of formula (I) comprises coupling of a carboxylic acid of formula (II):

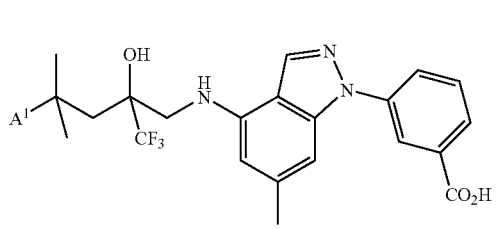
(II)

wherein $A^1$ is as defined above for compounds of formula (I) with an amine $HN(R^2)C(R^3)(R^4)CONHR^5$ or

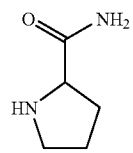

wherein $R^2$, $R^3$, $R^4$ and $R^5$ are as defined above for compounds of formula (I).

This coupling may be conducted, for example, using HATU (O-(7-azabenzotriazol-1-yl)-N,N,N'N'-tetramethyluronium hexafluorophosphate) in the presence of a suitable base such as N,N-diisopropylethylamine in a suitable solvent such as DMF. The coupling may also be conducted using alternative, conventional conditions for amide bond formation known in the art.

Alternatively compounds of formula (I) may be prepared from the carboxylic acid (II) by two sequential amide couplings firstly with the amino acid $HN(R^2)C(R^3)(R^4)CO_2H$ or D- or L-proline followed by a second coupling with $R^5$—$NH_2$, for example ammonia, wherein $R^2$, $R^3$, $R^4$ and $R^5$ are as defined above for compounds of formula (I).

The carboxylic acid (II) may be obtained by deprotection of a suitable protected derivative (III)

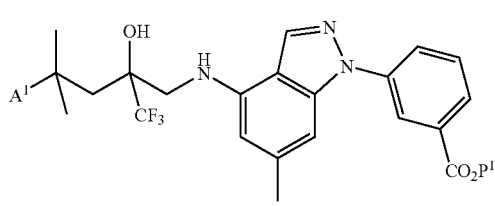
(III)

wherein $A^1$ is as defined above for compounds of formula (I) and $P^1$ represents a suitable ester protecting group, for example a benzyl ester or methyl ester. In the case of the benzyl protecting group, deprotection may be conveniently conducted by hydrogenolysis over palladium on carbon in ethanol. In the case of the methyl ester protecting group, deprotection may be conveniently conducted by base hydrolysis using for example sodium or potassium hydroxide in aqueous methanol. Alternative protecting groups suitable for use according to the present invention are well known to those skilled in the art and may be used in a conventional manner. See, for example, "Protective groups in organic synthesis" by T. W. Greene and P. G. M. Wuts (John Wiley & sons 1999) or "Protecting Groups" by P. J. Kocienski (Georg Thieme Verlag 1994).

Intermediates of formula (III) may be obtained by reaction of an epoxide of formula (IV):

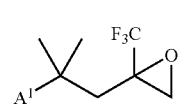
(IV)

wherein $A^1$ is as defined above for compounds of formula (I), with a 4-amino-1-arylindazole of formula (V):

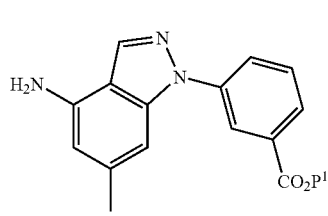
(V)

wherein $P^1$ is an ester protecting group as defined above for compounds of formula (III).

The epoxide opening reaction may be performed, for example, by heating the epoxide (IV) and aminoindazole (V) in acetonitrile solution at 85° C. in the presence of ytterbium (III) triflate as catalyst (*Synthetic Communications* 2003, 33, 2989-2994 and *Bioorg. Med. Chem. Letters.* 2001, 11, 1625-1628). Yttrium(III) triflate may also be utilised as catalyst for this reaction. Other catalysts which may be used include, for example, zinc triflate, scandium triflate, copper triflate and triflic acid.

The compound of formula (IV) wherein $A^1$ represent 5-fluoro-2-methoxy-phenyl is described in racemic form in WO04/063163 and has also been described as separate enantiomers in US2005/0234250, WO05/040145, *Bioorg. Med. Chem. Letters.* 2006, 16, 654-657 and in *J Org. Chem.* 2007, 72, 292-294.

Compounds of formula (V) are novel and form another aspect of the invention and may be prepared by reaction of 6-methyl-1H-indazol-4-amine (VI):

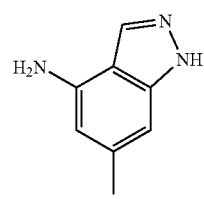
(VI)

with aryl iodides of formula (VII)

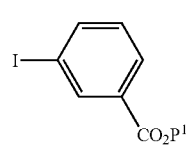
(VII)

wherein $P^1$ is an ester protecting group as defined for compounds of formula (III).

The reaction of (VI) with (VII) may be performed in the presence of a copper(I) catalyst, such as copper(I) iodide and a weak base such as potassium carbonate or potassium phosphate and an amine ligand such as L-proline, cyclohexanediamine, N,N'-dimethylcyclohexanediamine or N,N'-dimethylethylenediamine in a variety of solvents including toluene, dioxane, N,N-dimethylformamide, N,N-dimethylacetamide and dimethylsulfoxide at a temperature in the range 60-160° C., most typically 110° C. Representative procedures are reported in the literature: Synthesis 2005, 3, 496-499, *J. Org. Chem.*, 2004, 69, 5578-5587 and *J. Am. Chem. Soc.*, 2001, 123, 7727-7729.

Alternatively, compounds of formula (V) may be prepared by similar reaction of 6-methyl-4-nitro-1H-indazole (VIII)

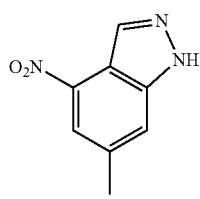

(VIII)

with the aryl iodides (VII) followed by reduction of the nitro group by, for example, hydrogenation over palladium on carbon.

6-Methyl-1H-indazol-4-amine (VI) and 6-methyl-4-nitro-1H-indazole (VIII) are known compounds which may be prepared, for example, using methods described in the literature: *J. Chem. Soc.*, 1955, 2412-2423 and references cited therein.

An alternative process according to the invention for the preparation of compounds of formula (III) comprises reaction of an amine of formula (IX):

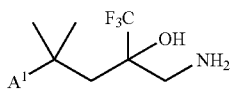

(IX)

wherein $A^1$ is as defined above for compounds of formula (I) with a 4-bromo-1-arylindazole of formula (X):

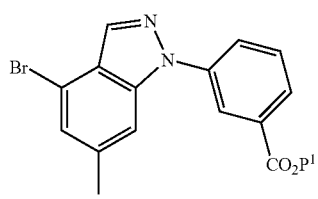

(X)

wherein $P^1$ is an ester protecting group as defined above for compounds of formula (III).

This coupling reaction may be conveniently carried out using palladium catalysis of the type described by Buchwald in *Topics in Current Chemistry*, 2002, 219, 131-209. For example, the coupling reaction may be conducted using tris(dibenzylideneacetone)dipalladium(0), racemic BINAP (2,2'-bis(diphenylphosphino)-1,1'-binaphthyl) and sodium tert-butoxide in toluene at reflux temperature or using microwave heating.

The compound of formula (IX) wherein $A^1$ represents 5-fluoro-2-methoxy-phenyl is known in racemic form (WO 05/003098, WO 03/082827). Compounds of formula (IX) may also be prepared by opening epoxides of formula (IV) with benzylamine followed by removal of the benzyl group by hydrogenolysis using, for example, palladium on carbon as catalyst.

Individual enantiomers of compounds of formula (IX) may be obtained, for example, by separation by HPLC on a chiral column of the racemic material (IX) or a protected version (XI) thereof;

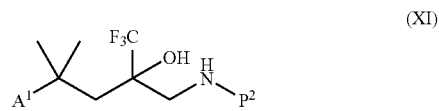

(XI)

wherein the group $A^1$ is as defined above for compounds of formula (I), and $P^2$ represents a protecting group which is removed following enantiomer separation.

In one embodiment, $P^2$ represents a benzyloxycarbonyl (CBZ), or benzyl protecting group. However, those skilled in the art could envisage the use of other protecting groups as alternatives. The CBZ or benzyl protecting groups may be removed by, for example, hydrogenolysis over a suitable catalyst such as palladium on carbon.

Where this protecting group $P^2$ in compound (XI) contains an additional chiral centre of defined stereochemistry, for example, in the (R)-1-phenylethylamine derivative (XII)

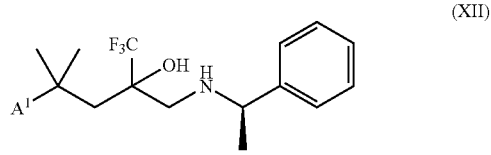

(XII)

wherein the group $A^1$ are as defined above for compounds of formula (I), the resulting diastereoisomers may be separated by chromatography on a non-chiral or chiral support. As Before, Deprotection by Hydrogenolysis Following Isomer Separation Provides the Single enantiomers of compound (IX).

Compounds of formula (XI) may be prepared directly by protection of the racemic amine (IX). Alternatively intermediates of formula (XI) and (XII) may be prepared by the reaction of the epoxide (IV) with an amine $P^2$—$NH_2$.

The epoxide opening reaction may be performed, for example, by heating with the amine in ethanol solution at 50-80° C.

Compounds of formula (X) are novel and form another aspect of the invention and may be prepared by cyclisation of a hydrazone of formula (XIII)

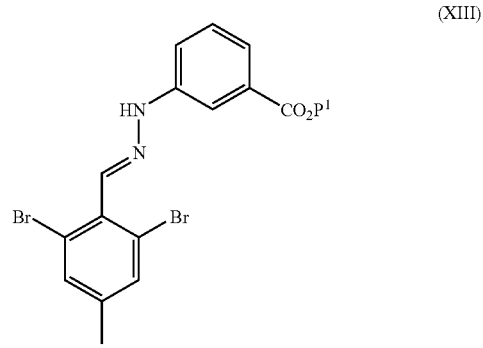

(XIII)

wherein P¹ is an ester protecting group as defined for compounds of formula (III). Alternatively, compounds of formula (X) may be obtained by cyclisation of the carboxylic acid (XIII, P¹=H) followed by ester protection.

This intramolecular N-arylation may be conducted using palladium catalysis of the type described by Buchwald in *Topics in Current Chemistry*, 2002, 219, 131-209. For example, the cyclisation may be effected using tris(dibenzylideneacetone)dipalladium(0), racemic-BINAP (2,2'-bis(diphenylphosphino)-1,1'-binaphthyl) and tripotassium phosphate in toluene or 1,4-dioxane at reflux temperature. Alternatively this cyclisation may be conducted in the absence of palladium using for example lithium bis(trimethylsilyl)amide in a suitable solvent for example a mixture of DMF and THF.

The 4-bromo-1-arylindazole carboxylic acid (X, P¹=H) may also conveniently be employed to provide 4-amino-1-arylindazoles intermediates of formula (V). For example, treatment of the 4-bromoindazole (X, P₁=H) with aqueous ammonia under pressure in the presence of copper (I) iodide catalyst provides the 4-amino-1-arylindazoles (V, P¹=H).

Hydrazones of formula (XIII) may be prepared by reaction of the aldehyde (XIV)

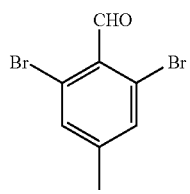

(XIV)

with an aryl hydrazine of formula (XV)

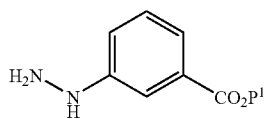

(XV)

wherein P¹ is ester protecting group as defined for compounds of formula (III). Alternatively the aldehyde (XIV) may be reacted with the unprotected carboxylic acid (XV, P¹=H) to give the hydrazone acid (XIII, P¹=H) which may either be esterified and then cyclised to give the indazole (X) or cyclised followed by ester protection to give indazole (X).

The aldehyde (XIV) is known and may be prepared as described by Lulinski and Serwatowski in *J. Org. Chem.*, 2003, 68, 5384-5387

Aryl hydrazines (XV) are either commercially available or may be prepared from the corresponding aniline by treatment with nitrous acid generated in situ from sodium nitrite followed by subsequent reduction of the resulting aryldiazonium ions with tin(II) chloride according to standard literature procedures (see, for example, *J Med Chem* 1991, 34, 2895; *J Med Chem* 2000 43: 4707, *J Med Chem* 2003 46: 2012).

Compounds of formula (I) in which A1 represents 5-fluoro-2-hydroxy-phenyl may be prepared by reaction of the compounds of formula (I) in which A1 represents 5-fluoro-2-methoxy-phenyl with, for example, boron tribromide in dichloromethane solution or by treatment with lithium iodide in N-methylpyrrolidinone using microwave heating at 220° C.

Compounds of formula (I) may be prepared in the form of mixtures of enantiomers or diastereoisomers when mixtures of isomers are used as intermediates in the synthesis. For example, the use of a compound of formula (IV) or (IX) as a racemic mixture of enantiomers will lead to a mixture of isomers in the final product. These isomers may, if desired, be separated by conventional methods (e.g. HPLC on a chiral column or by resolution with a chiral reagents, for example a chiral acid or a chiral amine).

Alternatively, separation of isomers may be performed earlier in the synthesis, for example individual isomers of compounds of formula (IV) or (IX) may be employed which may obviate the need to perform a separation of isomers as a final stage in the synthesis. The latter process is, in theory, more efficient and is therefore preferred. The intermediate epoxide (IV) in which A¹ represents 5-fluoro-2-methoxy-phenyl may for example be conveniently obtained in homochiral form by separation of the enantiomers of the precursor hydroxy acid (XVI)

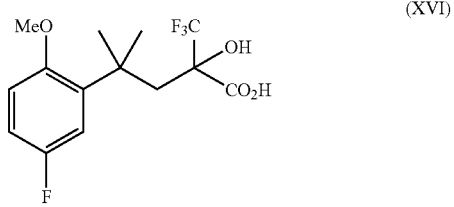

(XVI)

Compositions comprising a compound of the invention also constitute an aspect of the invention.

In addition, processes for preparing compositions including one or more compounds of formula (I) form an aspect of this invention.

Solvates of compounds of formula (I), physiologically functional derivatives thereof or salts thereof, which are not physiologically acceptable may be useful as intermediates in the preparation of other compounds of formula (I), physiologically functional derivatives thereof or salts thereof.

Compounds of the invention may be expected to demonstrate good anti-inflammatory and/or anti-allergic properties. They also may be expected to have an attractive side-effect profile, demonstrated, for example, by increased selectivity for the glucocorticoid receptor over the progesterone receptor and are expected to be compatible with a convenient regime of treatment in human patients.

The invention will now be illustrated by way of the following non-limiting examples.

EXAMPLES

Synthetic Experimental

| Abbreviations | |
|---|---|
| CDCl₃ | Deuterochloroform |
| DMSO | Dimethylsulphoxide |
| EtOH | Ethanol |
| Me | Methyl |
| NMR | Nuclear magnetic resonance |
| SPE | Solid phase extraction |
| HPLC | High pressure liquid chromatography |
| LCMS | Liquid chromatography mass spectrometry |
| DMF | N,N-Dimethylformamide |

-continued

| Abbreviations | |
|---|---|
| BINAP | (2,2'-Bis(diphenylphosphino)-1,1'-binaphthyl) |
| HATU | O-(7-Azabenzotriazol-1-yl)-N,N,N',N'-tetramethyluronium hexafluorophosphate |
| HCl | Hydrochloric acid |
| EtOAc | Ethyl acetate |
| TBME | t-Butyl methyl ether (1,1-dimethylethyl methyl ether) |
| DCM | Dichloromethane |
| TFA | Trifluoroacetic acid |
| THF | Tetrahydrofuran |
| IMS | Industrial methylated spirit |

Chromatographic Purification

Chromatographic purification was performed using pre-packed silica gel cartridges. The Flashmaster II is an automated multi-user flash chromatography system, available from Argonaut Technologies Ltd, which utilises disposable, normal phase, SPE cartridges (2 g to 100 g). It provides quaternary on-line solvent mixing to enable gradient methods to be run. Samples are queued using the multi-functional open access software, which manages solvents, flow-rates, gradient profile and collection conditions. The system is equipped with a Knauer variable wavelength UV-detector and two Gilson FC204 fraction-collectors enabling automated peak cutting, collection and tracking.

NMR $^1$H NMR spectra were recorded in either CDCl$_3$ or DMSO-d$_6$ on either a Bruker DPX 400 or Bruker Avance DRX or Varian Unity 400 spectrometer all working at 400 MHz. The internal standard used was either tetramethylsilane or the residual protonated solvent at 7.25 ppm for CDCl$_3$ or 2.50 ppm for DMSO-d$_6$.

Mass Directed Autopreparative HPLC

System A:

Agilent 1100 series LC/MSD hardware, using electrospray positive mode (ES +ve) running chemstation 32 purification software.

Column: Zorbax Eclipse XDB-C18 prep HT (dimensions 212×100 mm, 5 μm packing), 20 ml/min solvent speed.

Aqueous solvent=Water+0.1% TFA

Organic solvent=MeCN+0.1% TFA

Specific Gradients Used:

Gradient 1 (collects on UV/Mass Ion Trigger)

1 min 70% Water (0.1% TFA): 30% MeCN (0.1% TFA) increasing over 9 mins to 5% Water (0.1% TFA): 95% MeCN (0.1% TFA) to elute compounds.

Gradient 2 (Collects on UV Only)

1 min 70% Water (0.1% TFA): 30% MeCN (0.1% TFA) increasing over 9 mins to 5% Water (0.1% TFA): 95% MeCN (0.1% TFA) to elute compounds.

System B:

Carried out using a Micromass ZQ platform. The column was a 100 mm×20 mm Supelco LCABZ++ with stationary phase particle size of 5 μm.

| Solvents: | A: water + 0.1% formic acid |
| | B: MeCN:water 95:5 + 0.05% formic acid |
| Gradient | 50-90% B over 10 minutes |
| Flow rate | 20 mL/min |

LCMS System

The LCMS system used was as follows:

Column: 3.3 cm×4.6 mm ID, 3 μm ABZ+PLUS from Supelco

Flow Rate: 3 ml/min

Injection Volume: 5 μl

Temp: RT

UV Detection Range: 215 to 330 nm

| Solvents: | A: 0.1% Formic Acid + 10 mMolar Ammonium Acetate. | | |
| | B: 95% Acetonitrile + 0.05% Formic Acid | | |
| | Time | A % | B % |
| Gradient: | 0.00 | 100 | 0 |
| | 0.70 | 100 | 0 |
| | 4.20 | 0 | 100 |
| | 5.30 | 0 | 100 |
| | 5.50 | 100 | 0 |

Circular Dichroism

Circular dichroism was carried out on an Applied Photophysics Chirascan spectrophotometer at room temperature, using acetonitrile as solvent, over the range 200-350 nm.

Intermediate 1: Phenylmethyl
3-(4-amino-6-methyl-1H-indazol-1-yl)benzoate

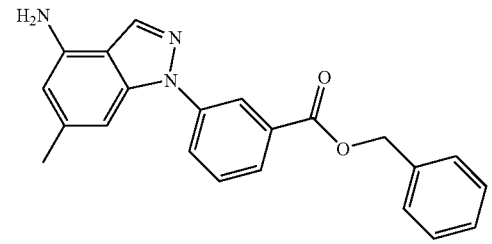

a) Preparation of phenylmethyl 3-iodobenzoate

3-Iodobenzoic acid (12.4 g) was dissolved in DMF (100 mL) and potassium carbonate (7.6 g) was added. Benzyl bromide (6.5 mL) was then added dropwise over approximately 10 minutes causing a slight exotherm to 24° C. The suspension was stirred at room temperature for 1.5 hours. The suspension was then poured into water (approximately 300 mL) and was extracted with diethyl ether. The combined organic phase was back washed with water and brine and dried over sodium sulfate. The solvent was stripped to yield a crude product as a colourless oil (17.0 g). The crude product was applied to a silica gel column and was eluted with cyclohexane-ethyl acetate (95:5) to give a colourless oil (13.08 g).

$^1$H NMR (400 MHz, CDCl$_3$) 8.41 (1H, t), 8.05 (1H, dt), 7.90 (1H, dt), 7.48-7.34 (5H, m), 7.19 (1H, t) and 5.37 (2H, s)

b) Preparation of phenylmethyl 3-(4-amino-6-methyl-1H-indazol-1-yl)benzoate

6-Methyl-1H-indazol-4-amine hydrochloride (0.5 g, 2.7 mmol), phenylmethyl 3-iodobenzoate (0.9 g, 2.6 mmol), copper (I) iodide (14 mg, 0.07 mmol), potassium carbonate (1.2 g, 8.68 mmol) and trans-N,N'-dimethyl-1,2-cyclohexanediamine (20 mg, 0.14 mmol) were heated together in DMF (5 mL) at reflux overnight. The mixture was poured into water (15 mL) and ethyl acetate was added to dissolve the resulting oil. The suspension was then filtered through celite. The organic phase was separated, combined with a second ethyl acetate extract, washed successively with water and brine and then dried over anhydrous sodium sulphate and evaporated under reduced pressure. The residue was purified by silica gel column chromatography (75 g) eluting with 1 to 5% gradient of ethyl acetate in dichloromethane to give the title compound as a light brown oil (0.3 g).

$^1$H-NMR: (CDCl$_3$, 400 MHz) δ 8.46 (t, 1H), 8.10 (s, 1H), 8.06 (m, 1H), 7.96 (m, 1H), 7.61 (t, 1H), 7.49 (m, 2H), 7.42 (m, 2H), 7.38 (m, 1H), 6.96 (s, 1H), 6.31 (s, 1H), 5.44 (s, 2H), 4.15 (m, 2H), 2.42 (s, 3H)

Intermediate 2: Phenylmethyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate

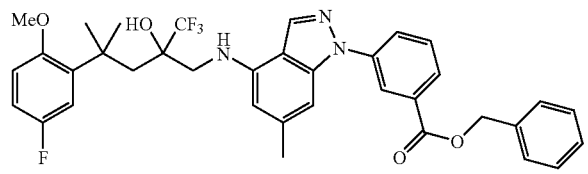

A solution of racemic 2-{2-[5-fluoro-2-(methyloxy)phenyl]-2-methylpropyl}-2-(trifluoromethyl)oxirane (which may be prepared according to WO 04/063163, 350 mg, 1.2 mmol), in acetonitrile (2 mL) was added to a mixture of phenylmethyl 3-(4-amino-6-methyl-1H-indazol-1-yl)benzoate (357 mg, 1.0 mmol) and ytterbium(III) triflate (124 mg, 0.2 mmol). The mixture was stirred and heated to 85° C. under nitrogen in a greenhouse apparatus for 18 hours when the temperature was raised to 100° C. and the mixture heated under vigorous reflux for a further ~21 hours. The mixture was cooled to room temperature and partitioned between dichloromethane (50 mL) and aqueous sodium bicarbonate (50 mL). The aqueous layer was extracted again with dichloromethane (50 mL) and the combined organic extracts were dried over anhydrous sodium sulphate and evaporated. The residue was purified by silica gel chromatography using the Flashmaster II (50 g cartridge) eluting with a cyclohexane to 1:1 cyclohexane:ethyl acetate gradient over 40 minutes to give the title compound as a white solid (424 mg).

$^1$H-NMR: (CDCl$_3$, 400 MHz) δ 8.40 (t, 1H), 8.04-8.07 (m, 1H), 7.97 (s, 1H), 7.91 (ddd, 1H), 7.60 (t, 1H), 7.46-7.49 (m, 2H), 7.35-7.43 (m, 4H), 7.17 (dd, 1H), 6.91-6.99 (m, 2H), 6.85 (dd, 1H), 5.70 (broad s, 1H), 5.42 (s, 2H), 3.87 (s, 3H), 3.35 (d, 1H), 3.12 (d, 1H), 2.88 (d, 1H), 2.38 (s, 3H), 2.28 (d, 1H), 1.46 (s, 3H), 1.43 (s, 3H)

Intermediate 3: 3-(4-{[4-[5-Fluoro-2-(methyloxy)phenyl]-2-hydroxy-4-methyl-2-(trifluoromethyl)pentyl]amino}-6-methyl-1H-indazol-1-yl)benzoic acid

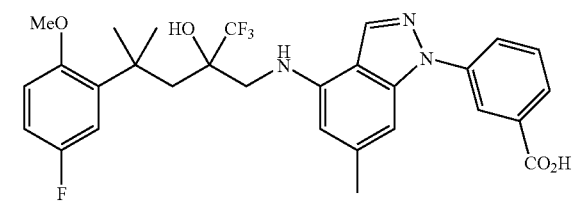

Method A: Via Benzyl Ester

Phenylmethyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate (2.33 g, 3.59 mmol) was suspended in ethanol (75 mL) and hydrogenated with vigorous stirring at 5 atmospheres at room temperature in the presence of 10% palladium on carbon (700 mg) for 16 hours. The mixture was filtered through Celite and the filtrate evaporated to provide the title compound as a pale yellow foam (1.85 g).

LCMS: $t_{RET}$=4.06 min; MH$^+$=560

Method B: Via Methyl Ester

Methyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate (440 mg, 0.77 mmol) was stirred in 10% potassium hydroxide in methanol (3 mL) at 40° C. The starting material dissolves as the reaction proceeds and the hydrolysis was complete in 1.5 h as indicated by HPLC. The reaction mixture was then allowed to cool to room temperature and the pH adjusted to 1 using 5M HCl. Water (3 mL) was added and the precipitated product was collected by filtration and dried under vacuum at 40° C. over the weekend to give the title compound as a solid (352 mg).

LCMS: $t_{RET}$=3.92 min; MH$^+$=560

Method C: Two Step procedure from 2-{2-[5-fluoro-2-(methyloxy)phenyl]-2-methylpropyl}-2-(trifluoromethyl)oxirane 2-{2-[5-Fluoro-2-(methyloxy)phenyl]-2-methylpropyl}-2-(trifluoromethyl)oxirane (344.2 g, 1.18 mol) was added to acetonitrile (1.375 L), followed by the addition of methyl 3-(4-amino-6-methyl-1H-indazol-1-yl)benzoate (333.3 g, 1.18 mol) and yttrium trifluoromethanesulfonate (126.6 g, 0.236 mol, 20 mol %). The resulting mixture was heated to reflux (83° C.) for 17 hours 40 minutes and was then allowed to cool to 20±3° C. Hydrochloric acid (0.75M, 3.42 L) was then added followed by TBME (1.7 L). The aqueous phase was removed and the organic phase was filtered through celite. The filter was washed with TBME (690 mL) and the combined organic filtrate was washed again firstly with 0.75M hydrochloric acid (2×3.42 L) and then with saturated brine (2.6 L) and filtered through celite. Methanol (2.8 L) was added and the mixture concentrated down to 2.76 L by distilling off the TBME. The mixture was allowed to cool down to 40±3° C., and potassium hydroxide (345 g) was added. The hydrolysis of the methyl ester was complete in ca. 1 hour and water (3.45 L) was then added and the pH was adjusted to ca.1 using 5M hydrochloric acid. The product was extracted into TBME (2 L) and the extract was finally washed with saturated brine (2.6 L) and filtered through celite. The filter was washed with TBME (0.69 L) and the combined filtrates were concentrated to dryness and the product was dried in vacuo at 40° C. to give the title compound (517.7 g).

LCMS: $t_{RET}$=3.93 min; MH$^+$=560

Intermediate 4: N-{[3-(4-{[4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-N-methyl-L-almandine

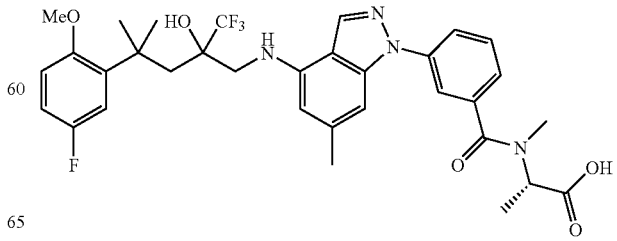

N,N-Diisopropylethylamine (0.149 mL, 0.855 mmol) and HATU (68.3 mg, 0.18 mmol) were added to a solution of 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid (96 mg, 0.171 mmol) in DMF (1 mL) and the solution stirred at room temperature under nitrogen for 10 min. N-methyl-L-almandine (44.1 mg, 0.43 mmol) was added and the mixture stirred at room temperature for 5 days. The resulting suspension was diluted with methanol and DMSO to give a solution which was filtered and purified by mass directed autopreparation (System B) to give the title compound (40.9 mg).

LCMS: $t_{RET}$=3.79 min; MH$^+$=645

Intermediate 5: N-{[3-(4-{[4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-N-methyl-D-almandine

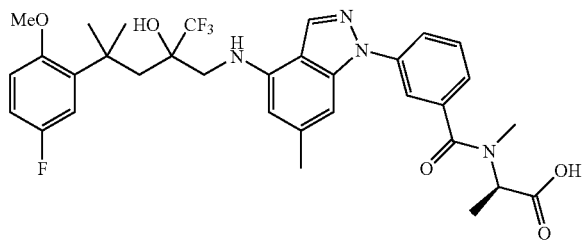

Prepared similarly to Intermediate 4 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and N-methyl-D-almandine.

LCMS: $t_{RET}$=3.80 min; MH$^+$=645

Intermediate 6: N-{[3-(4-{[4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-serine

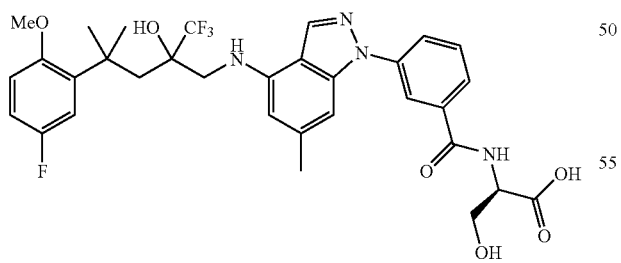

Prepared similarly to Intermediate 4 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and D-serine.

LCMS: $t_{RET}$=3.84 min; MH$^+$=647

Intermediates 7 and 8: Phenylmethyl[4-[5-fluoro-2-(methyloxy)phenyl]-2-hydroxy-4-methyl-2-(trifluoromethyl)pentyl]carbamate

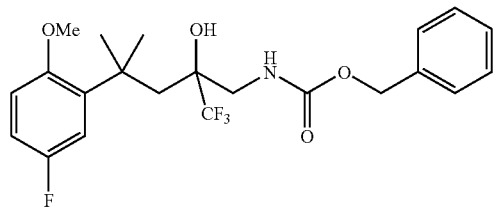

Racemic 2-(aminomethyl)-1,1,1-trifluoro-4-[5-fluoro-2-(methyloxy)phenyl]-4-methyl-2-pentanol (which may be prepared according to WO03/082827, 894 mg, 2.89 mmol) was dissolved in dichloromethane (15 mL). N-(benzyloxycarbonyloxy)succinimide (1.08 g, 4.34 mmol) was added and the mixture was stirred for 5 min. Triethylamine (804 µL, 5.78 mmol) was added and stirring was continued for 3.5 hours after which time the reaction mixture was washed with saturated sodium bicarbonate solution and evaporated in vacuo. Purification of the residue by Flashmaster II using a 10 g silica cartridge and a solvent gradient of cyclohexane:EtOAc 100:0 to 0:100 over a period of 1 hour gave the racemic product as an oil (1.12 g). This oil was applied to a 2 inch×20 cm Chiralpak AD column eluted with heptane:IPA 97.5:2.5 with a flow rate of 75 mL/min to give Intermediate 7 (2R isomer, 443 mg) after ca. 42 min and Intermediate 8 (2S isomer, 441 mg) after ca. 60 min.

Intermediate 7 (2R isomer): Analytical chiral HPLC (25× 0.46 cm Chiralpak AD column, heptane:IPA 97.5:2.5 eluting at 1 mL/min): ca. 8 min LCMS: $t_{RET}$=3.75 min; MH$^+$=444.

Intermediate 8 (2S isomer): Analytical chiral HPLC (25× 0.46 cm Chiralpak AD column, heptane:IPA 97.5:2.5 eluting at 1 mL/min): ca.9.8 min LCMS: $t_{RET}$=3.75 min; MH$^+$=444.

Intermediates 9 and 10: 1,1,1-Trifluoro-4-[5-fluoro-2-(methyloxy)phenyl]-4-methyl-2-({[(1R)-1-phenylethyl]amino}methyl)-2-pentanol

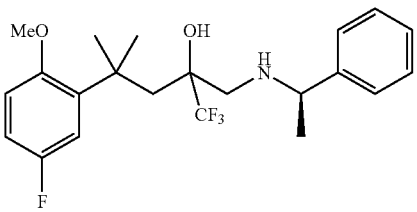

To a stirred solution of racemic 2-{2-[5-fluoro-2-(methyloxy)phenyl]-2-methylpropyl}-2-(trifluoromethyl)oxirane (which may be prepared according to WO04/063163, 600 mg, 2.05 mmol) in anhydrous EtOH (3 mL) was added (R)-(+)-1-phenylethylamine (1.31 mL, 10.3 mmol). The reaction mixture was then stirred and heated at 50° C. under nitrogen overnight and then for 5 days, cooled to room temperature and evaporated in vacuo. The residue was applied to a 70 g silica SPE cartridge and eluted with 0.5% NH$_3$ in toluene. The appropriate fractions were combined and evaporated in vacuo to give a colourless oil (991.4 mg). 710 mg of this oil was separated by chiral HPC on a 2 inch×15 cm Chiralpak AD column eluted with 25% acetonitrile/0.25M ammonium phosphate (pH 4.9) with a flow rate of 70 mL/min to give Intermediate 9 (2S isomer, 230 mg) after 17.5 min and Intermediate 10 (2R isomer, 200 mg) after 24.8 min.

Intermediate 9 (2S isomer):

Single crystal X-ray structure on an orthorhombic crystal obtained by slow evaporation from ethyl acetate established the 2S configuration.

LCMS: $t_{RET}$=2.81 min; MH$^+$=414

Intermediate 10 (2R isomer):

LCMS: $t_{RET}$=2.91 min; MH$^+$=414

Intermediate 11: (2R)-2-(Aminomethyl)-1,1,1-trifluoro-4-[5-fluoro-2-(methyloxy)phenyl]-4-methyl-2-pentanol

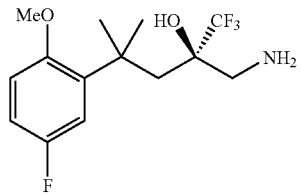

Method A: Via (2R)-phenylmethyl[4-[5-fluoro-2-(methyloxy)phenyl]-2-hydroxy-4-methyl-2-(trifluoromethyl)pentyl]carbamate (2R)-Phenylmethyl[4-[5-fluoro-2-(methyloxy)phenyl]-2-hydroxy-4-methyl-2-(trifluoromethyl)pentyl]carbamate (343 mg, 0.774 mmol) was dissolved in EtOH (25 mL) and hydrogenated over 10% palladium on charcoal (34 mg) at room temperature and 3 bar for 4 hours. The catalyst was removed by filtration through celite and the filtrate was evaporated in vacuo to give the title compound as a grey solid (213 mg) which was used without further purification.

LCMS: $t_{RET}$=2.38 min; MH$^+$=310

Circular Dichroism (Cell Length: 0.5 cm; Concentration: 230 μM)

221.0 nm (de=−1.25) and 280.4 nm (de=−0.76)

Method B: Via (2R)-1,1,1-trifluoro-4-[5-fluoro-2-(methyloxy)phenyl]-4-methyl-2-({[(1R)-1-phenylethyl]amino}methyl)-2-pentanol (2R)-1,1,1-Trifluoro-4-[5-fluoro-2-(methyloxy)phenyl]-4-methyl-2-({[(1R)-1-phenylethyl]amino}methyl)-2-pentanol (200 mg, 0.48 mmol) was dissolved in EtOH (8 mL) and hydrogenated over 10% palladium on charcoal (100 mg) at 53 psi and room temperature for 16 hours. Catalyst was removed by filtration through celite. The celite was washed several times with EtOH. The filtrate was evaporated in vacuo to give the title compound as a pale yellow oil (158 mg) which was used without further purification.

LCMS: $t_{RET}$=2.38 min; MH$^+$=310

Circular Dichroism (Cell Length: 0.5 cm; Concentration: 230 μM)

222.0 nm (de=−0.96) and 280.8 nm (de=−0.69)

Intermediate 12: 3-{2-[(2,6-Dibromo-4-methylphenyl)methylidene]hydrazino}benzoic acid

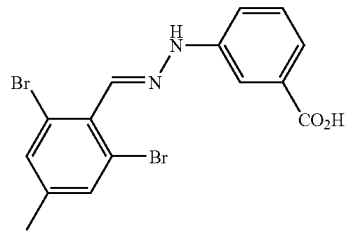

Method A:

2,6-Dibromo-4-methylbenzaldehyde (14.74 g, 53 mmol) and 3-hydrazinobenzoic acid (8.07 g, 53 mmol) were suspended in methanol (250 mL) and heated at reflux under nitrogen for 2 hours. The mixture was cooled to room temperature and then cooled in ice and the precipitate was collected by filtration, washed with ice-cold methanol (approximately 2×50 mL) and dried in vacuo to afford the title compound (19.8 g).

LCMS: $t_{RET}$=4.07 min; MH$^+$=411/413/415

Method B:

2,6-Dibromo-4-methylbenzaldehyde (1500 g, 5.39 mol) and 3-hydrazinobenzoic acid (820.2 g, 5.39 mol) were suspended in methanol (12.75 L) under a nitrogen atmosphere and heated to 40° C. After 2 hrs, heating was stopped and the reaction mixture was cooled to 0° C. and stirred for 30 min. The precipitate was filtered and washed with chilled methanol (1.5 L) and dried in vacuo at 55° C. to afford the title compound (2121.8 g).

LCMS: $t_{RET}$=3.96 min; MH$^+$=411/413/415

Intermediate 13: Phenylmethyl 3-{2-[(2,6-dibromo-4-methylphenyl)methylidene]hydrazino}benzoate

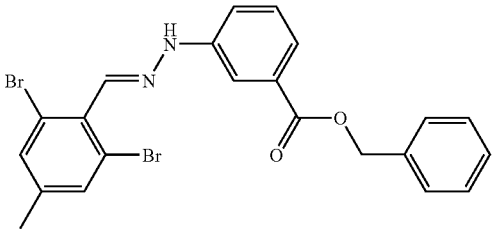

Potassium carbonate (7.41 g, 53.61 mmol) was added to a solution of 3-{2-[(2,6-dibromo-4-methylphenyl)methylidene]hydrazino}benzoic acid (19.4 g, 44.65 mmol) in dry DMF (200 mL). Benzyl bromide (5.42 mL, 45.6 mmol) was then added and the mixture stirred at room temperature for 15 hours and then partitioned between ethyl acetate (500 mL) and water (500 mL). The organic phase was separated, combined with a second ethyl acetate extract (300 mL), washed successively with water (4×500 mL) and brine (300 mL), dried over anhydrous sodium sulphate, evaporated and further dried under vacuum to give the title compound (23.2 g).

LCMS: $t_{RET}$=4.51 min; MH$^+$=501, 503, 505

Intermediate 14: Phenylmethyl
3-(4-bromo-6-methyl-1H-indazol-1-yl)benzoate

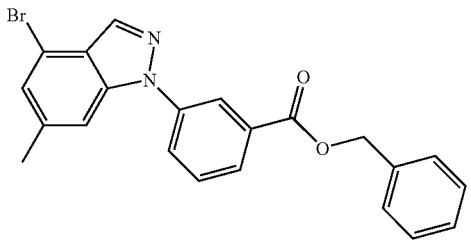

Phenylmethyl 3-{2-[(2,6-dibromo-4-methylphenyl)methylidene]hydrazino}benzoate (10.04 g, 20 mmol), tripotassium phosphate (10.61 g, 50 mmol), tris(dibenzylideneacetone)dipalladium(0) (575 mg, μmol) and racemic BINAP (623 mg, μmol) were dissolved in dioxane (200 mL) and heated under reflux for 48 hours in a nitrogen atmosphere. The mixture was then cooled and partitioned between dichloromethane and dilute hydrochloric acid (ca 300 mL of each). The organic phase was separated, dried over anhydrous sodium sulphate and evaporated. The crude product was combined with material obtained from a similar reaction (8.9 g input of phenylmethyl 3-{2-[(2,6-dibromo-4-methylphenyl)methylidene]hydrazino}benzoate) and purified by silica gel chromatography using the Flashmaster II (2×50 g cartridges) eluting with a 100:0 to 0:100 cyclohexane:dichloromethane gradient over 40 minutes. Product containing fractions were combined and evaporated to leave a brown oil which on stirring with diethyl ether solidified. Washing with ether (3×15 mL) provide the title compound as a beige solid (10.2 g).

LCMS: $t_{RET}$=4.37 min; MH$^+$=421/423

Intermediate 15: Phenylmethyl 3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)benzoate

A mixture of (2R)-2-(aminomethyl)-1,1,1-trifluoro-4-[5-fluoro-2-(methyloxy)phenyl]-4-methyl-2-pentanol (54.7 mg, 0.177 mmol), phenylmethyl 3-(4-bromo-6-methyl-1H-indazol-1-yl)benzoate (65.3 mg, 0.155 mmol), tris(dibenzylideneacetone)dipalladium(0) (14.2 mg, 0.0155 mmol), racemic-BINAP (9.7 mg, 0.0155 mmol) and sodium tert-butoxide (20.9 mg, 0.217 mmol) in anhydrous toluene (0.9 mL) was heated in a microwave reactor at 120° C. (power set at 400 Watts, 30 seconds pre-stirring) for 15 min. The reaction mixture was filtered and the filtrate was partitioned between water and ethyl acetate (40 mL of each). The organic phase was separated, washed with brine, dried through a hydrophobic frit and evaporated and purified by mass directed autopreparation (System B). Product containing fractions were partitioned between dichloromethane and aqueous sodium bicarbonate. The aqueous layer was re-extracted with dichloromethane and the combined organic extracts were washed successively with water and brine, dried through a hydrophobic frit and evaporated in vacuo to give the title compound (18.8 mg).

LCMS: $t_{RET}$=4.31 min; MH$^+$=650

Intermediate 16: 3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)benzoic acid

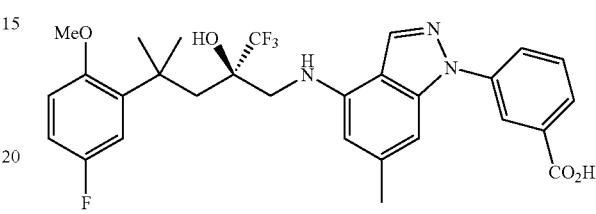

Method A:
Phenylmethyl 3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)benzoate (18.8 mg, 0.029 mmol) in methanol (0.6 mL) was hydrogenated at 50 atmospheres at 25° C. over 10% palladium on carbon (700 mg) using an H-cube. The methanol was evaporated to give the impure title compound (11.9 mg) which was used without further purification.

LCMS: $t_{RET}$=4.03 min; MH$^+$=560

Method B:
A solution of methyl 3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)benzoate (400 mg, 0.7 mmol) in methanol (16 mL) was stirred at room temperature. A solution of 2M sodium hydroxide (5 mL) was added and the resulting mixture was stirred at room temperature overnight. The pH was then adjusted to ca. 1 using 1M HCl to form an off-white suspension which was extracted into TBME (15 mL). The organic phase was then washed successively with saturated sodium bicarbonate (10 mL) and saturated brine (10 mL). The organic phase was then dried over anhydrous sodium sulphate and concentrated to give the title compound as a solid (331 mg).

LCMS: $t_{RET}$=3.91 min; MH$^+$=560

Intermediate 17: 4-[5-Fluoro-2-(methyloxy)phenyl]-2-hydroxy-4-methyl-2-(trifluoromethyl)pentanoic acid

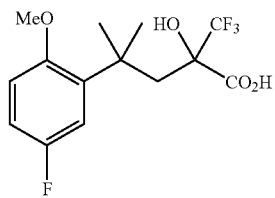

Manganese (109.2 g, 1.99 mol) was suspended in dry THF (630 mL) and treated with a solution of 0.5M zinc chloride in THF (168 mL) and the mixture heated under reflux. 3-Bromo- 2-methyl-1-propene (20.1 mL, 20.8 mmol) was added at reflux (contents at 66° C.) followed by a THF (14 mL) line wash. This mixture was then stirred for 57 min. A solution of 3-bromo-2-methyl-1-propene (207 g, 1.53 mol) and ethyl 3,3,3-trifluoro-2-oxopropanoate (140 g, 0.82 mol) was dissolved in THF (560 mL) under a $N_2$ atmosphere and then added at 3 ml/min to the mixture under reflux. When 10% of this solution was added the batch was cooled to 50° C. and the addition was stopped and analysed by $^{19}F$ NMR to check for formation of ethyl 2-hydroxy-4-methyl-2-(trifluoromethyl)-4-pentenoate. The remaining 90% of the above solution was then added over 4 h at reflux*. The mixture was then heated under reflux for 1 hour and then the jacket set to 20° C. and the mixture stirred at 20° C. overnight. (*The addition of 3-bromo-2-methyl-1-propene and ethyl 3,3,3-trifluoro-2-oxopropanoate in THF was found to be highly exothermic and could potentially lead to hazardous vessel pressurization. This reaction is most safely conducted by initiating the reaction by adding a small amount of 3-bromo-2-methyl-1-propene at reflux and then cooling to 55° C. before adding the remaining material, with multiple sampling and monitoring by NMR to ensure accumulation of ethyl 3,3,3-trifluoro-2-oxopropanoate does not reach unsafe levels).

The reaction mixture was diluted with ethyl acetate (1400 mL) and then cooled to 0° C. (jacket set at 0° C.). A solution of 27% w/v of ammonium chloride (700 mL) was added over 24 min and the resulting emulsion was stirred at below 4.9° C. for 56 min. 5M Hydrochloric acid (700 mL) was added at between 1 and 5° C. over 54 min. The biphasic mixture was then stirred at 5° C. for 20 min and the phases separated at 5° C. A sample of the upper organic phase was analysed by $^{19}F$ and $^1H$ NMR to check for formation of ethyl 2-hydroxy-4-methyl-2-(trifluoromethyl)-4-pentenoate. The solution was left standing for 1 hour 11 min. The organic phase was washed successively with 25% w/v aqueous brine (560 mL), 9% w/v aqueous sodium bicarbonate (560 mL) and 25% w/v aqueous brine (560 mL) and left standing overnight at 20° C. The organic phase was then concentrated to 560 mL by atmospheric distillation. 1-Fluoro-4-(methyloxy)benzene (518 g, 4.1 mol) was added and the solution placed under medium vacuum and on achieving 150 mbar the mixture was heated to 87° C. very slowly. The mixture was then concentrated to 630 mL and maintained at a vacuum of 135 mbar and temperature of 90° C. for 1.2 hours then the vacuum was released before cooling to 20° C. (Ethyl 2-hydroxy-4-methyl-2-(trifluoromethyl)-4-pentenoate was not isolated but was used directly in the next stage).

Aluminum chloride (231 g, 1.73 mol) was added to the mixture in five equal portions with intervals of 10 min maintaining the temperature at 20-50° C. during this addition. The mixture was then stirred at 20° C. for overnight and the mixture was then cooled to 1° C. (jacket set at −2° C.) and quenched with slow addition of IMS (140 mL) at 3±3° C. over 1 hour, TBME (840 mL) was then added at 5±5° C. over 20 min and then water (840 mL) was added at 5±5° C. over 1 hour 20 min. The resulting biphasic mixture was stirred at 5±5° C. for 10 min and the phases separated. The organic phase was washed successively with 0.5M HCl (560 mL) and 9% w/v aqueous sodium bicarbonate (560 mL) at 5±5° C. (Ethyl-4-[5-fluoro-2-(methyloxy)phenyl]-2-hydroxy-4-methyl-2-(trifluoromethyl)pentanoate was not isolated but was used directly in the next stage).

The organic phase containing ethyl 4-[5-fluoro-2-(methyloxy)phenyl]-2-hydroxy-4-methyl-2-(trifluoromethyl)pentanoate was concentrated to 590 mL by atmospheric distillation before diluting with methanol (2800 mL), the vessel was then cooled (jacket set at 60° C.). The jacket was then set at 20° C. and left to stand overnight. This solution was then re-concentrated by atmospheric distillation at 80° C. to 1120 mL before cooling to 20° C. Potassium hydroxide flakes (231 g, 4.1 mol) were added in two equal portions with stirring, with an interval of 10 min of stirring between each addition maintaining the temperature at 20-50° C. The suspension was then heated at reflux for 53 min and then cooled to 20° C. and diluted with water (1260 mL). The aqueous methanolic solution was washed with toluene (2×840 mL) and the aqueous phase containing the potassium salt of 4-[5-fluoro-2-(methyloxy)phenyl]-2-hydroxy-4-methyl-2-(trifluoromethyl)pentanoic acid was separated and left standing overnight. The aqueous phase was then diluted with TBME (700 mL) before adjusting the pH to 1 by the slow addition 5M HCl (875 mL) over 45 min at a temperature of 20±5° C. (jacket was set at 15° C.). The mixture was then stirred for 20 min and the phases were then separated. The organic phase was washed with 25% w/v aqueous brine (560 mL) and then diluted with iso-octane (2100 mL) and concentrated to 840 mL by atmospheric distillation. TBME (140 mL) was then added and the resulting solution was applied to a silica column (238 g, pre-eluted with a mixture of iso-octane/TBME (6:1, 980 mL)) and eluted with iso-octane/TBME (6:1, 1960 mL). Product containing fractions were diluted with further iso-octane (980 mL) before concentrating to 1680 mL by atmospheric distillation. The solution was cooled to 54° C. and seeded with crystals of 4-[5-fluoro-2-(methyloxy)phenyl]-2-hydroxy-4-methyl-2-(trifluoromethyl)pentanoic acid (21 mg). Crystallization ensued after 5 min and the resulting suspension was stirred at 53° C. for 30 min before cooling to 20° C., it was then left to stand over the weekend. The suspension was then stirred at 20° C. for 20 min and the product collected by filtration and washed with iso-octane (2×210 mL) at 20° C. The product was dried in vacuo at 40° C. for 24 hours to afford the title compound as an off-white crystalline solid (136.1 g).

LCMS: $t_{RET}$=1.02 min; MH$^-$=323

146 g of similarly prepared racemic material was separated into its enantiomers by chiral HPLC using a Varian SD-2 800G Prep HPLC system set-up with a 50 mm i.d.×244 mm preparative HPLC column packed with Chiralpak AD 20 micron chiral stationary phase. The racemate was dissolved in 95:5:0.05 heptane:ethanol:trifluoroacetic acid (typically 8.5 g in 80 mL) for injection onto the column. The column was eluted with 95:5:0.05 heptane:ethanol:trifluoroacetic acid at a flow rate of 118 mL/min. The first eluting 2S enantiomer was collected as a fraction eluting typically between 4.2 min and 6.0 min. A mixed fraction was collected eluting typically from 6.0 min to 6.6 min. The second eluting 2R enantiomer was collected in a fraction eluting typically between 6.6 min and 10 min. Mixed fractions being evaporated and reprocessed by the same method. Evaporation of fractions containing the first eluting enantiomer provided Intermediate 17-A (2S)-4-[5-fluoro-2-(methyloxy)phenyl]-2-hydroxy-4-methyl-2-(trifluoromethyl)pentanoic acid as a solid (66 g) containing <0.5% of the opposite enantiomer. Evaporation of fractions containing the second eluting enantiomer were evaporated to provide Intermediate 17-B (2R)-4-[5-fluoro-2-(methyloxy)phenyl]-2-hydroxy-4-methyl-2-(trifluoromethyl)pentanoic acid as a solid (64 g) containing <0.5% of the opposite enantiomer.

Intermediate 17-A (2S-enantiomer) Analytical chiral HPLC (25×0.46 cm Chiralpak AD column, 95:5:0.05 heptane:ethanol:trifluoroacetic acid, eluting at 1 mL/min, column temperature 20° C.): $t_{RET}$=5.2 min Intermediate 17-B (2R-enantiomer) Analytical chiral HPLC (25×0.46 cm Chiralpak AD column, 95:5:0.05 hep-

Intermediate 18: (2R)-4-[5-Fluoro-2-(methyloxy) phenyl]-4-methyl-2-(trifluoromethyl)-1,2-pentanediol

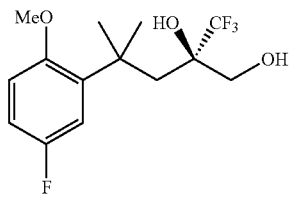

A solution of lithium aluminium hydride (1M in tetrahydrofuran, 12.6 mL, 12.6 mmol) was introduced into a flask under a nitrogen atmosphere. The solution was heated to 50° C. under nitrogen. (2R)-4-[5-fluoro-2-(methyloxy)phenyl]-2-hydroxy-4-methyl-2-(trifluoromethyl)pentanoic acid (2 g, 6.17 mmol) in tetrahydrofuran (4 mL) was then added dropwise using a syringe pump (50 mL/h addition rate). The solution was then stirred for 13 h at 50° C. The reaction mixture was then cooled to 0° C. and quenched with a slow addition (10 mL/h addition rate) of water (0.5 mL) keeping the temperature below 5 C. Once gas evolution stopped, the cloudy solution was allowed to warm to 20° C. and 15% aqueous sodium hydroxide solution (0.5 mL) followed by water (1.5 mL) were added dropwise (40 mL/h addition rate). The slurry was stirred for 15 min at room temperature, filtered and the inorganic salts were washed twice with ethyl acetate (2×10 mL). The organic liquors were then washed successively with 7.5% aqueous sodium bicarbonate solution (20 mL) and saturated brine (20 mL). The organic liquor was split into two equal amounts, the first half was concentrated to dryness to afford the title compound (851 mg) and the second half was re-crystallised from methyl-cyclohexane to afford the title compound (595 mg).

LCMS (before recrystallisation): $t_{RET}$=3.26 min; $MH^+$=311

Intermediate 19: (2R)-2-{2-[5-Fluoro-2-(methyloxy) phenyl]-2-methylpropyl}-2-(trifluoromethyl)oxirane

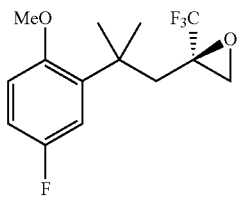

Triethylamine (8.2 mL, 58.8 mmol) was added to a solution of (2R)-4-[5-fluoro-2-(methyloxy)phenyl]-4-methyl-2-(trifluoromethyl)-1,2-pentanediol (3.4 g, 10.9 mmol) in DCM (34 mL). This solution was then cooled to 0° C. and neat methanesulphonyl chloride (1.1 mL, 15.3 mmol) was added over 5 min keeping the temperature at 0-5° C. The resulting suspension was stirred at 0-5° C. for 15 min before warming to 20° C. The reaction mixture was then left to stir overnight. Further neat methanesulphonyl chloride (0.84 μL, 0.1 eq) was added at room temperature and the mixture stirred for 15 min. The reaction mixture was then washed successively with 1M HCl (3×12 mL), 9% aqueous sodium bicarbonate (12 mL) and water (12 mL) before evaporating to dryness to afford the title compound, 3.08 g.

Analytical chiral HPLC (25×0.46 cm Chiralcel OD-H column, 100% heptane eluting at 1 mL/min, column temp 30° C.): $t_{RET}$=5.5 min purity 99.8% (2S enantiomer $t_{RET}$=5.1 min)

Intermediate 20: 3-(4-Bromo-6-methyl-1H-indazol-1-yl)benzoic acid

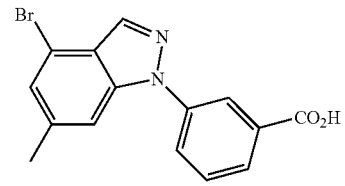

A solution of 3-{2-[(2,6-dibromo-4-methylphenyl)methylidene]hydrazino}benzoic acid (1050 g) in DMF (3.46 L) was cooled to 10° C. under nitrogen. Lithium bis(trimethylsilyl)amide solution (1M in THF, 6.34 L) was then added while maintaining the temperature below 15° C. The stirred solution was heated at 70±3° C. for 64 hrs and then the reaction mixture was cooled to 5° C. and quenched sequentially with the slow addition of water (4.2 L), 5M hydrochloric acid (2.62 L) and water (3.68 L). The resulting slurry was stirred at 5° C. for 1 hr 34 min, filtered and washed successively with purified water (1 L and then 2.1 L at 5±5° C.) and methanol (2×1 L at 5±5° C.). The solid was dried in vacuo at 50° C. to afford the title compound (742.9 g).

LCMS: $t_{RET}$=3.71 min; $MH^+$=331, 333

Intermediate 21: 3-(4-Amino-6-methyl-1H-indazol-1-yl)benzoic acid

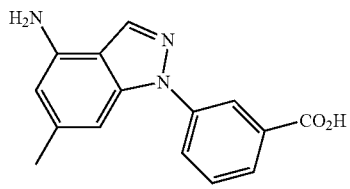

A suspension of 3-(4-bromo-6-methyl-1H-indazol-1-yl) benzoic acid (1450.5 g, 4.38 mol) and copper (I) iodide (42.47 g, 0.22 mol, 5 mol %) in aqueous ammonia (0.88 sg, 13.5 L) was heated in a sealed pressure vessel until a pressure of 7 Bar±0.3 Bar was generated (contents temperature ~78° C.). Stirring was continued for a period of ca. 2 days. The reaction mixture was cooled to 20° C. and then charged in to a Controlled Lab Reactor fitted with a 5M HCl scrubber. The solution was heated at reflux to remove excess ammonia by gradually raising the contents temperature to >90° C.—end point pH 7.87. The reaction mixture was then cooled to 60±3° C. and acetic acid (725 mL, 12.7 mol) was added slowly to form a precipitate—end point pH=5.68. The batch was cooled to 5±3° C. and stirred for 825 minutes. The slurry was filtered and washed with water (3×4.5 L). The solid was dried in vacuo at 50° C. to afford the title compound (1112.3 g).

LCMS: $t_{RET}$=2.93 min; $MH^+$=268

Intermediate 22: Methyl 3-(4-amino-6-methyl-1H-indazol-1-yl)benzoate

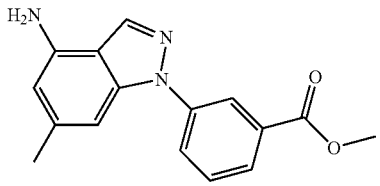

Acetyl chloride (1000 mL, 11.5 mol) was added slowly to cold methanol (10.84 L at 0±3° C.), under an atmosphere of nitrogen, while maintaining the temperature below 5° C. The reaction mixture was stirred for a further 35 min at 0±3° C. and then 3-(4-amino-6-methyl-1H-indazol-1-yl)benzoic acid (1084.2 g, 4.06 mol) was added. The reaction mixture was heated at reflux for 2.5 h and then the volume was reduced by distillation to approximately half the volume. Isopropyl acetate (10.84 L) was added maintaining the temperature at above 50° C. and the temperature held at 60° C. for 1 hour. The solution was cooled to 0° C. over a period of 3 hours and aged at 3±3° C. for a further ca. 10 hours. The precipitate was filtered and washed with a mixture of chilled isopropyl acetate:methanol (ca. 10:1, 3.26 L at 3±3° C.) and then chilled isopropyl acetate (2.1 L at 3±3° C.). The solid was dried in vacuo at 55° C. to afford the title compound as its hydrochloride salt (933.2 g): LCMS: $t_{RET}$=3.20 min; MH$^+$=282.min. A proportion of this material (874.1 g, 2.76 mol) in a mixture of water (5.28 L) and 2-methyltetrahydrofuran (8.7 L) was treated with sodium hydroxide (1M, 2720 mL then 2M, 13 mL) (until pH=7 is reached). The organic phase was separated and washed with water (6.1 L) and the aqueous layer extracts back extracted with 2-methyltetrahydrofuran (4.4 L). The combined organic extracts were evaporated to near dryness and then toluene (4.4 L) was added and the mixture evaporated to afford the title compound (767.4 g).

LCMS: $t_{RET}$=3.17 min; MH$^+$=282.

Intermediate 23: Methyl 3-(4-{[4-[5-fluoro-2-(methyloxy)phenyl]-2-hydroxy-4-methyl-2-(trifluoromethyl)pentyl]amino}-6-methyl-1H-indazol-1-yl)benzoate

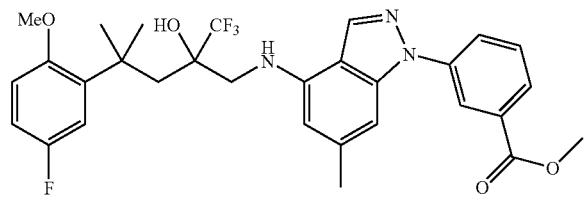

2-{2-[5-Fluoro-2-(methyloxy)phenyl]-2-methylpropyl}-2-(trifluoromethyl)oxirane (which may be prepared according to WO 04/063163, 96 mg, 0.33 mmol), methyl 3-(4-amino-6-methyl-1H-indazol-1-yl)benzoate (85 mg, 0.3 mmol) and ytterbium trifluoromethanesulfonate (28 mg, 0.045 mmol) were stirred in acetonitrile (0.4 mL) with some molecular sieves. The resulting mixture was then heated to reflux (80° C.) overnight and then allowed to cool to room temperature. The mixture was poured into ethyl acetate (5 mL) and washed successively with saturated aqueous sodium bicarbonate and aqueous brine. The organic phase was separated, dried over anhydrous sodium sulphate and then concentrated and the residue purified by silica gel column chromatography (10% ethyl acetate in cyclohexane) to give the title compound as a white solid (75 mg).

LCMS: $t_{RET}$=4.08 min; MH$^+$=574

Intermediate 24: Methyl 3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)benzoate

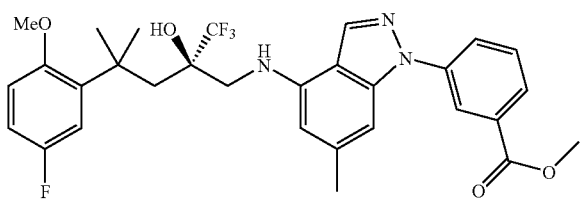

(2R)-2-{2-[5-Fluoro-2-(methyloxy)phenyl]-2-methylpropyl}-2-(trifluoromethyl)oxirane (530 mg, 1.81 mmol) was added to acetonitrile (2.5 mL), followed by the addition of methyl 3-(4-amino-6-methyl-1H-indazol-1-yl)benzoate (590 mg, 2.1 mmol) and yttrium trifluoromethanesulfonate (197 mg, 0.37 mmol) at room temperature under a nitrogen atmosphere. The resulting mixture was then heated to reflux (83° C.) overnight, then allowed to cool down to room temperature and diluted with ethyl acetate (7 mL). The mixture was washed successively with saturated sodium bicarbonate (10 mL) and water (10 mL), dried and concentrated. The residue was then purified by column chromatography (10% ethyl acetate in cyclohexane) to give, after concentration, the title compound (540 mg).

LCMS: $t_{RET}$=4.08 min; MH$^+$=574

Example 1

N-(2-Amino-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide

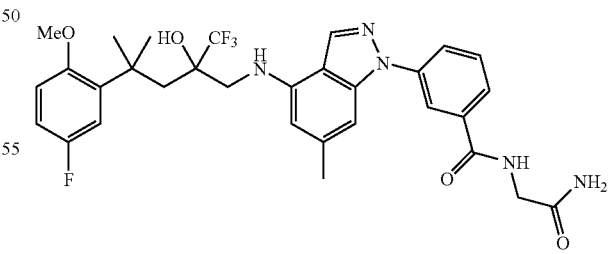

N,N-Diisopropylethylamine (0.109 mL, 0.625 mmol) was added to a solution of 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid (70 mg, 0.125 mmol) and HATU (47.5 mg, 0.125 mmol) in DMF (2.5 mL) and the solution stirred at room temperature for 5 min. Glycine hydrochloride (34.6 mg, 0.313 mmol) was added and the mixture stirred at room temperature overnight and then partitioned between 2M HCl (50 mL) and ethyl acetate (50 mL). The organic layer was separated, washed with aqueous sodium bicarbonate (50 ml), dried over anhydrous sodium sulphate and evaporated to give crude product which was purified by mass directed autopreparation (System B) to give the title compound (62.5 mg).

LCMS: $t_{RET}$=3.59 min; MH$^+$=616

This racemic material was resolved by chiral HPLC on a 2 inch×20 cm Chiralpak AD column eluted with heptane:EtOH 2:8 with a flow rate of 75 mL/min to provide Example 1-A (enantiomer A, 15.2 mg) and Example 1-B (enantiomer B, 17.5 mg)

Example 1-A (enantiomer A): Analytical chiral HPLC (25×0.46 cm Chiralpak AD column, heptane:EtOH 2:8 eluting at 1 mL/min): $t_{RET}$=6.7 min LCMS: $t_{RET}$=3.60 min; MH$^+$=616

Example 1-B: (enantiomer B) Analytical chiral HPLC (25×0.46 cm Chiralpak AD column, heptane:EtOH 1:9 eluting at 1 mL/min): $t_{RET}$=11.3 min LCMS: $t_{RET}$=3.60 min; MH$^+$=616

Example 2

N-(2-Amino-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)-N-methylbenzamide

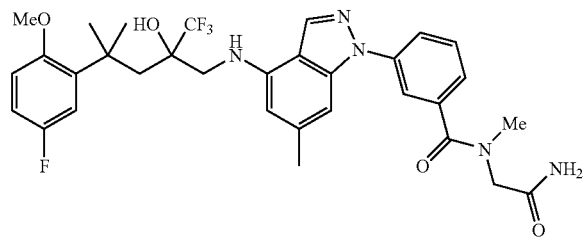

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and sarcosinamide hydrochloride.

LCMS: $t_{RET}$=3.57 min; MH$^+$=630

86.2 mg of this racemic material was resolved by chiral HPLC on a 2 inch×20 cm Chiralpak AD column eluted with heptane:EtOH 4:6 with a flow rate of 75 mL/min to provide Example 2-A (enantiomer A, 28.7 mg) and Example 2-B (enantiomer B. 31.5 mg)

Example 2-A: (enantiomer A) Analytical chiral HPLC (25×0.46 cm Chiralpak AD column, heptane:EtOH 4:6 eluting at 1 mL/min): $t_{RET}$=10.9 min LCMS: $t_{RET}$=3.58 min; MH$^+$=630

Example 2-B: (enantiomer B) Analytical chiral HPLC (25×0.46 cm Chiralpak AD column, heptane:EtOH 4:6 eluting at 1 mL/min): $t_{RET}$=19.1 min LCMS: $t_{RET}$=3.58 min; MH$^+$=630

Example 3

N-[(1R)-2-Amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide

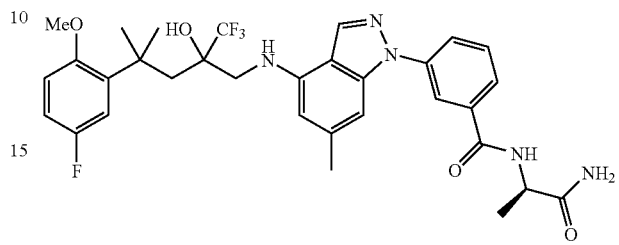

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and D-alaninamide hydrochloride.

LCMS: $t_{RET}$=3.65 min; MH$^+$=630

95.8 mg of this mixture of diastereomers was resolved by chiral HPLC on a 2 inch×20 cm Chiralpak AD column eluted with heptane:EtOH 2:8 with a flow rate of 75 mL/min to provide Example 3-A (diastereomer A, 42.4 mg) and Example 3-B (diastereomer B. 45.2 mg)

Example 3-A: (diastereomer A) Analytical chiral HPLC (25×0.46 cm Chiralpak AD column, heptane:EtOH 2:8 eluting at 1 mL/min): $t_{RET}$=5.1 min LCMS: $t_{RET}$=3.66 min; MH$^+$=630

Example 3-B: (diastereomer B) Analytical chiral HPLC (25×0.46 cm Chiralpak AD column, heptane:EtOH 2:8 eluting at 1 mL/min): $t_{RET}$=10.9 min LCMS: $t_{RET}$=3.66 min; MH$^+$=630

Example 4

N-[(1S)-2-Amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide

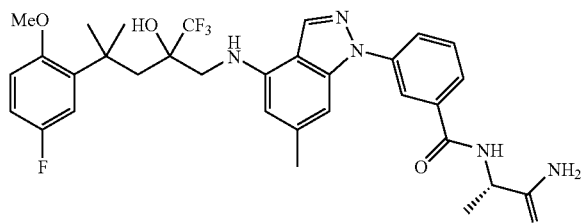

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and L-alaninamide hydrochloride with System A used for purification by mass directed autopreparation.

LCMS: $t_{RET}$=3.53 min; MH$^+$=630

Example 5

N-(2-Amino-1,1-dimethyl-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide

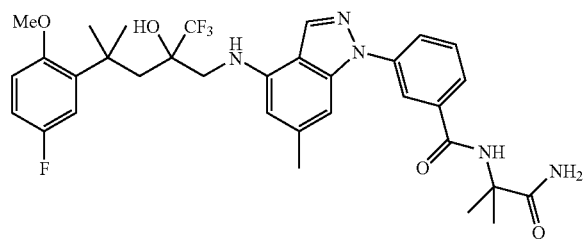

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and 2-methylalaninamide.

LCMS: $t_{RET}$=3.70 min; $MH^+$=644

16 mg of this racemic material was resolved by chiral HPLC on a 25 cm×2 cm Chiralpak AD column eluted with heptane:EtOH 1:1 with a flow rate of 15 mL/min to provide Example 5-A (enantiomer A, 6.0 mg) and Example 5-B (enantiomer B, 5.2 mg)

Example 5-A: (enantiomer A) Analytical chiral HPLC (25×0.46 cm Chiralpak AD column, heptane:EtOH 1:1 eluting at 1 mL/min): $t_{RET}$=14.8 min LCMS: $t_{RET}$=3.58 min; $MH^+$=644

Example 5-B: (enantiomer B) Analytical chiral HPLC (25×0.46 cm Chiralpak AD column, heptane:EtOH 1:1 eluting at 1 mL/min): $t_{RET}$=23.8 min LCMS: $t_{RET}$=3.58 min; $MH^+$=644

Example 6

1-{[3-(4-{[4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-L-prolinamide

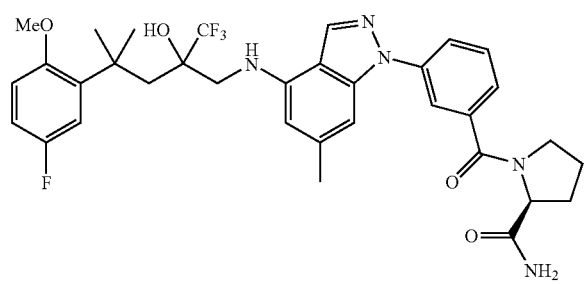

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and L-prolinamide with System A used for purification by mass directed autopreparation LCMS: $t_{RET}$=3.52 min; $MH^+$=656

Example 7

1-{[3-(4-{[4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide

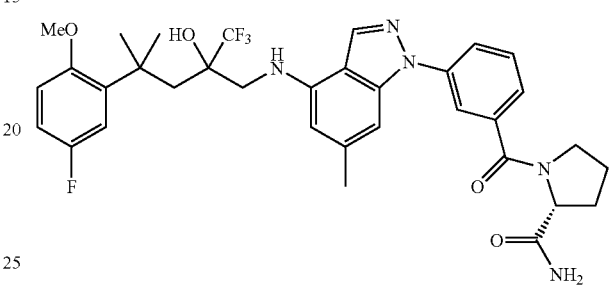

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and D-prolinamide.

LCMS: $t_{RET}$=3.63 min; $MH^+$=656

118.8 mg of this mixture of diastereomers was resolved by chiral HPLC on a 2 inch×20 cm Chiralpak AD column eluted with heptane:EtOH 1:9 with a flow rate of 75 mL/min to provide Example 7-A (diastereomer A, 59 mg) and Example 7-B (diastereomer B. 61 mg)

Example 7-A: (diastereomer A, 2R isomer) Analytical chiral HPLC (25×0.46 cm Chiralpak AD column, heptane:EtOH 1:9 eluting at 1 mL/min): $t_{RET}$=8.4 min LCMS: $t_{RET}$=3.63 min; $MH^+$=656

Example 7-B: (diastereomer B, 2S isomer) Analytical chiral HPLC (25×0.46 cm Chiralpak AD column, heptane:EtOH 1:9 eluting at 1 mL/min): $t_{RET}$=22.4 min LCMS: $t_{RET}$=3.63 min; $MH^+$=656

Example 7-A

1-{[3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide

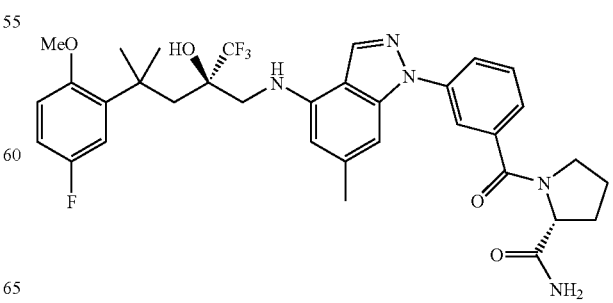

Method A:

N,N-Diisopropylethylamine (0.017 mL, 0.098 mmol), followed by HATU (7.8 mg, 0.02 mmol) were added to a solution 3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)benzoic acid (11 mg, 0.0196 mmol) in anhydrous DMF (0.3 mL) and the solution stirred at room temperature under nitrogen for 10 min. D-prolinamide (6 mg, 0.052 mmol) was added and the mixture stirred at room temperature overnight and then left in the fridge for 6 days. The resulting yellow solution was diluted with methanol to 0.5 mL and purified by mass directed autopreparation (System B). Product containing fractions were partitioned between dichloromethane and aqueous sodium bicarbonate. The aqueous layer was re-extracted with dichloromethane and the combined organic extracts were washed successively with water and brine, dried through a hydrophobic frit and evaporated to give the title compound (4.7 mg).

LCMS: $t_{RET}$=3.51 min; MH$^+$=656. Analytical chiral HPLC (25×0.46 cm Chiralcel OJ column, heptane:EtOH 4:1 eluting at 1 mL/min): $t_{RET}$=13.9 min. Using this same analytical chiral HPLC system the previously separated diastereomers of Example 7 showed $t_{RET}$=13.8 min (Example 7-A) and 20.9 min (Example 7-B).

Method B:

3-(4-{[4-[5-Fluoro-2-(methyloxy)phenyl]-2-hydroxy-4-methyl-2-(trifluoromethyl)pentyl]amino}-6-methyl-1H-indazol-1-yl)benzoic acid (464.3 g, 0.83 mol) was added to DMF (2.8 L) under nitrogen and the temperature adjusted to 20±3° C., followed by the addition of N,N-diisopropylethylamine (434 mL, 3 eq) and HATU (331 g, 1.05 eq). The resulting mixture was then stirred at 20±3° C. for ca. 1 hour. Then, D-prolinamide (115 g, 1.0 mol) was added and the resulting mixture was stirred at 20±3° C. until completion of the reaction (ca. 2 hours). Water (4.6 L) was added to the mixture and the product was extracted into TBME (3×2.8 L). The combined TBME extracts were washed with saturated brine (2×ca. 4.5 L) and were then concentrated to dryness under reduced pressure and finally dried at 40° C. under vacuum to give a mixture of the title compound and its 2S diastereomer (1-{[3-(4-{[(2S)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide) (512.1 g).

LCMS: $t_{RET}$=3.53 min; MH$^+$=656

86 g of similarly prepared material was separated into its diastereomers by chiral HPLC using a Varian SD-2 800G Prep HPLC system set-up with a 75 mm i.d.×250 mm preparative HPLC column packed with Chiralpak AD 20 micron chiral stationary phase. The racemate was dissolved in ethanol (batches of 1.5 g to 2.7 g in 15 mL) for injection onto the column. The column was eluted with 1:1 ethanol:methanol at a flow rate of 140 mL/min for approximately 15 to 18 min and then at 530 mL/min to elute the second eluting isomer. The first eluting 2R diastereomer was collected as a fraction eluting typically between 8.8 min and 14.6 min. Mixed fractions were collected eluting typically from 14.6 min and 16.2 min and these were evaporated and reprocessed using the same method. Evaporation of fractions containing the first eluting diastereomer were evaporated to provide 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (2R diastereomer, 39.7 g) containing 1% of the opposite diastereomer. 1-{[3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (2R diastereomer): Analytical chiral HPLC (25×0.46 cm Chiralpak AD-H column, 1:1 ethanol:methanol, eluting at 0.7 mL/min, column temperature 40° C.): $t_{RET}$=8.7 min (2S isomer $t_{RET}$=14.9 min).

A batch of similarly prepared 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide was recrystallised from toluene. 1-{[3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (221 g) was added to toluene (5.52 L) at 50±3° C. The solution was clarified and a line wash of toluene (440 mL) was added. The mixture was then stirred at 50±3° C. for 45 min before being cooled to 20±3° C. over ca. 1 hour. The slurry was aged at 20±3° C. for ca. 2 hours then cooled to 10±3° C. and aged for 95 min. The solid was filtered off under vacuum, washed with toluene (pre-filtered, 2×660 mL), and dried under vacuum at 80° C. to constant weight to give the title compound (181 g).

Melting point onset (DSC) 114° C.

LCMS: $t_{RET}$=3.52 min; MH$^+$=656

Characteristic XRPD angles and d-spacings are recorded in Table 1.

TABLE 1

| 2θ/° | d-spacing/Å |
| --- | --- |
| 5.7 | 15.4 |
| 7.1 | 12.4 |
| 8.2 | 10.7 |
| 10.0 | 8.9 |
| 10.8 | 8.2 |

Example 8

N-[(1S)-2-Amino-1-(hydroxymethyl)-2-oxoethyl]-3-(4-{[4-[5-fluoro-2-(methloxy)phenyl]-2-hydroxy-4-methyl-2-(trifluoromethyl)pentyl]amino}-6-methyl-1H-indazol-1-yl)benzamide

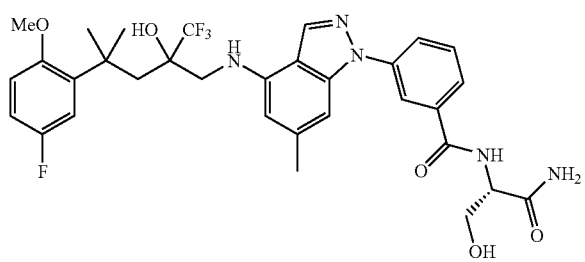

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and L-serinamide with System A used for purification by mass directed autopreparation.

LCMS: $t_{RET}$=3.40 min; MH$^+$=646

Example 9

N-(2-Amino-2-oxoethyl)-3-(4-{[4-(5-fluoro-2-hydroxyphenyl)-2-hydroxy-4-methyl-2-(trifluoromethyl)pentyl]amino}-6-methyl-1H-indazol-1-yl)-N-methylbenzamide

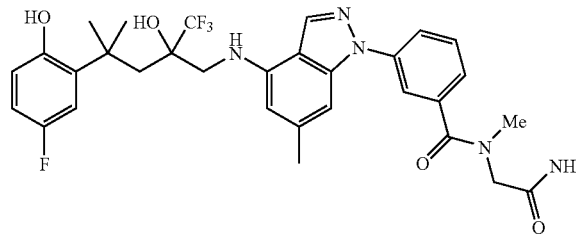

N-(2-Amino-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)-N-methylbenzamide (55.1 mg, 0.0875 mmol) was dissolved in anhydrous dichloromethane (0.2 mL) and cooled to −78° C. (cardice/acetone bath) under nitrogen. Boron tribromide (1.0M in dichloromethane) (0.435 mL, 0.435 mmol) was then added portionwise and after 5 minutes the mixture was allowed to warm to room temperature. The reaction was stirred at room temperature for 6 hours, re-cooled to −78° C. and quenched with methanol (1 mL). The reaction was warmed to room temperature when more dichloromethane (1 mL) and aqueous saturated sodium hydrogen carbonate solution (2 mL) were added and the mixture stirred vigorously and then poured onto a hydrophobic frit and the dichloromethane layer collected and evaporated in vacuo. This crude product was purified by mass-directed autopreparation (System B). Product containing fractions were combined and partitioned between dichloromethane and saturated aqueous sodium bicarbonate. The aqueous layer was re-extracted twice more with dichloromethane and the combined organic extracts were washed successively water and brine, dried through a hydrophobic frit and evaporated in vacuo to give the title compound (17.2 mg).

LCMS: $t_{RET}$=3.41 min; $MH^+$=616

Example 10

N-(2-Amino-2-oxoethyl)-3-(4-{[4-(5-fluoro-2-hydroxyphenyl)-2-hydroxy-4-methyl-2-(trifluoromethyl)pentyl]amino}-6-methyl-1H-indazol-1-yl)benzamide

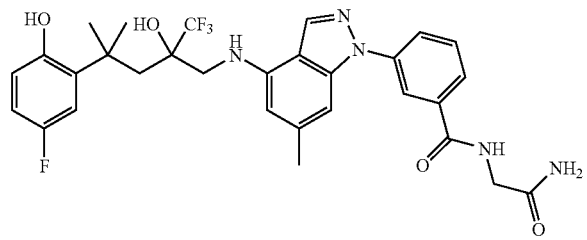

Prepared similarly to Example 9 from N-(2-amino-2-oxoethyl)-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide.

LCMS: $t_{RET}$=3.43 min; $MH^+$=602

Example 11

N-[(1R)-2-Amino-1-methyl-2-oxoethyl]-3-(4-{[4-(5-fluoro-2-hydroxyphenyl)-2-hydroxy-4-methyl-2-(trifluoromethyl)pentyl]amino}-6-methyl-1H-indazol-1-yl)benzamide

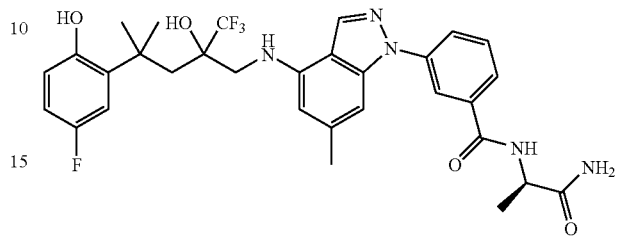

Prepared similarly to Example 9 from N-[(1R)-2-amino-1-methyl-2-oxoethyl]-3-(4-{[4-[5-fluoro-2-(methyloxy)phenyl]-2-hydroxy-4-methyl-2-(trifluoromethyl)pentyl]amino}-6-methyl-1H-indazol-1-yl)benzamide.

LCMS: $t_{RET}$=3.49 min; $MH^+$=616

Example 12

1-{[3-(4-{[4-(5-Fluoro-2-hydroxyphenyl)-2-hydroxy-4-methyl-2-(trifluoromethyl)pentyl]amino}-6-methyl-1H-indazol-1-yl)phenyl]carbonyl}-D-prolinamide

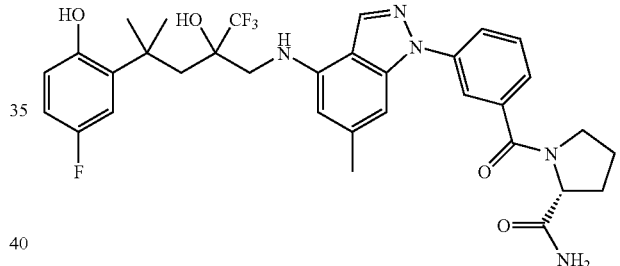

Prepared similarly to Example 9 from 1-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide except that after warming to room temperature the reaction was left overnight instead of for 6 hours.

LCMS: $t_{RET}$=3.32 min; $MH^+$=642

Example 13

3-(4-{[4-[5-Fluoro-2-(methyloxy)phenyl]-2-hydroxy-4-methyl-2-(trifluoromethyl)pentyl]amino}-6-methyl-1H-indazol-1-yl)-N-[2-(methylamino)-2-oxoethyl]benzamide

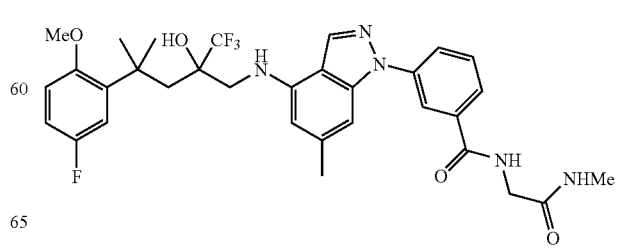

Prepared similarly to Example 1 from 3-(4-{[4-[5-fluoro-2-(methyloxy)phenyl]-2-hydroxy-4-methyl-2-(trifluoromethyl)pentyl]amino}-6-methyl-1H-indazol-1-yl)benzoic acid and N¹-methylglycinamide with System A used for purification by mass directed autopreparation.

LCMS: $t_{RET}$=3.54 min; MH⁺=630

Example 14

N-[(1S)-2-Amino-1-methyl-2-oxoethyl]-3-(4-{[4-[5-fluoro-2-(methloxy)phenyl]-2-hydroxy-4-methyl-2-(trifluoromethyl)pentyl]amino}-6-methyl-1H-indazol-1-yl)-N-methylbenzamide

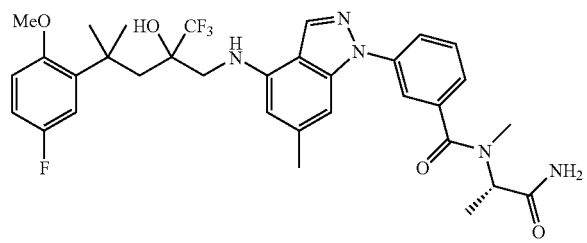

N,N-Diisopropylethylamine (0.044 mL, 0.25 mmol) and HATU (20.1 mg, 0.053 mmol) were added to a solution of N-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-N-methyl-L-almandine (32.4 mg, 0.05 mmol) in DMF (1 mL) and the solution stirred at room temperature under nitrogen for 10 min. Ammonia in dioxan (5M, 1.01 mL, 5.05 mmol) was added and the mixture stirred at room temperature overnight. The mixture was diluted with methanol and purified by mass directed autopreparation (System B) and product containing fractions were partitioned between dichloromethane and aqueous sodium bicarbonate. The organic phase was separated, combined with a second dichloromethane extract, washed twice with water, dried through a hydrophobic frit and evaporated to give the title compound (11 mg).

LCMS: $t_{RET}$=3.52 min; MH⁺=644

Example 15

N-[(1R)-2-Amino-1-methyl-2-oxoethyl]-3-(4-{[4-[5-fluoro-2-(methloxy)phenyl]-2-hydroxy-4-methyl-2-(trifluoromethyl)-pentyl]amino}-6-methyl-1H-indazol-1-yl)-N-methylbenzamide

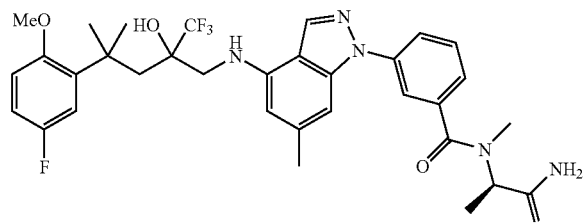

Prepared similarly to Example 14 from N-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-N-methyl-D-almandine and ammonia.

LCMS: $t_{RET}$=3.52 min; MH⁺=644

Example 16

N-[(1R)-2-Amino-1-(hydroxymethyl)-2-oxoethyl]-3-(4-{[4-[5-fluoro-2-(methloxy)phenyl]-2-hydroxy-4-methyl-2-(trifluoromethyl)pentyl]amino}-6-methyl-1H-indazol-1-yl)benzamide

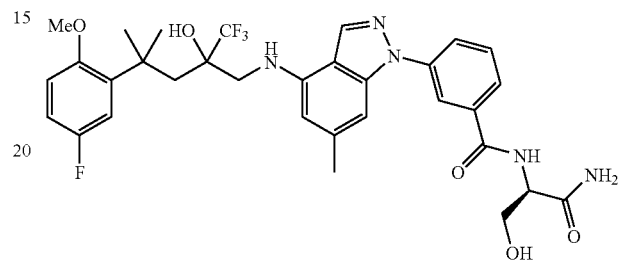

Prepared similarly to Example 14 from N-{[3-(4-{[4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-serine and ammonia.

LCMS: $t_{RET}$=3.41 min; MH⁺=646

Example 17

1-{[3-(4-{[(2R)-4-(5-Fluoro-2-hydroxyphenyl)-2-hydroxy-4-methyl-2-(trifluoromethyl)pentyl]amino}-6-methyl-1H-indazol-1-yl)phenyl]carbonyl}-D-prolinamide

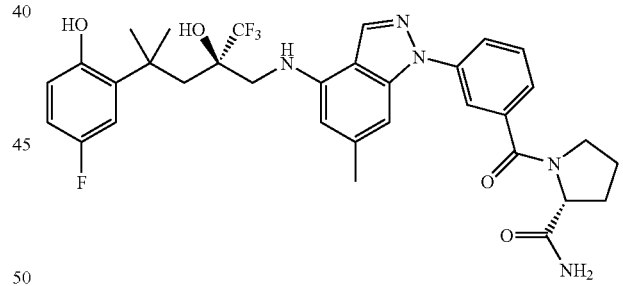

1-{[3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (340 mg, 0.5185 mmol) was dissolved in anhydrous dichloromethane (12 mL) and cooled to −78° C. (cardice/acetone bath) under nitrogen. Boron tribromide (1.0M in dichloromethane, 2.57 mL, 2.57 mmol) was then added portionwise and after 5 minutes the stirred mixture was allowed to warm slowly to room temperature under nitrogen. After 4 hours, LCMS suggested little reaction had occurred and the mixture was re-cooled to −78° C. and additional boron tribromide (1.0M in dichloromethane, 2 mL, 2 mmol) was added and the mixture was then stirred at room temperature overnight. LCMS still indicated the reaction was incomplete and the mixture was re-cooled to −78° C. once more and more boron tribromide (1.0M in dichloromethane, 2 mL, 2 mmol) was added and the mixture stirred at room temperature for 3 hours before being re-cooled to −78° C. and quenched by the gradual addition of methanol (5 mL). The reaction was warmed to room temperature when more dichloromethane (30 mL) and aqueous saturated sodium hydrogen carbonate solution (75 mL) were added and the mixture stirred vigorously for 5 minutes. The organic phase was separated by passing through a hydrophobic frit and evaporated in vacuo. This crude product was purified by mass-directed autopreparation. Product containing fractions were combined and partitioned between dichloromethane and saturated aqueous sodium bicarbonate. The organic layer was washed successively water and brine, dried through a hydrophobic frit and evaporated in vacuo to give the title compound (98 mg).

LCMS: $t_{RET}$=3.36 min; MH+=642

Polymorph Experimental

1-{[3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide in crystalline form was prepared by the following method:

Toluene (0.5 mL) was added to amorphous 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (25 mg) and the slurry was temperature cycled (0 to 40° C. in one hour blocks) for 2.5 days. The solid was isolated by forcing the solvent through a glass frit at room temperature under pressure and then left to air dry at ambient temperature for 1-2 days.

The resulting crystalline form was characterized using DSC (differential scanning calorimetry) and XRPD (X-ray powder diffraction).

Differential Scanning Calorimetry (DSC)

The DSC thermogram of crystalline 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide was obtained using a TA Q1000 calorimeter, serial number 1000-0126. The sample was weighed into an aluminium pan, a pan lid placed on top and lightly crimped without sealing the pan. The experiment was conducted using a heating rate of 10° C. min$^{-1}$.

The data are illustrated in FIG. 1.

X-Ray Powder Diffraction (XRPD)

The X-ray powder diffraction (XRPD) pattern of crystalline 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide is shown in FIG. 2. The data were acquired on a PANalytical X'Pert Pro powder diffractometer, model PW3040/60, serial number DY1850 using an XCelerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a Si wafer (zero background) plates, resulting in a thin layer of powder. Characteristic XRPD angles and d-spacings are recorded in Table 2.

Characteristic peaks for the solid state form are summarised in Table 2 with calculated lattice spacings. Peak positions were measured using Highscore software.

TABLE 2

| 2θ/° | d-spacing/Å |
|---|---|
| 4.1 | 21.7 |
| 5.7 | 15.5 |
| 7.1 | 12.4 |

TABLE 2-continued

| 2θ/° | d-spacing/Å |
|---|---|
| 8.2 | 10.8 |
| 9.0 | 9.8 |
| 10.0 | 8.9 |
| 10.7 | 8.2 |
| 11.4 | 7.8 |
| 12.8 | 6.9 |
| 13.4 | 6.6 |
| 14.1 | 6.3 |
| 14.5 | 6.1 |
| 15.6 | 5.7 |
| 17.6 | 5.0 |
| 18.0 | 4.9 |
| 18.7 | 4.7 |
| 20.6 | 4.3 |
| 21.0 | 4.2 |

Pharmaceutical Composition Experimental
Compositions for Intranasal Use

In the compositions below, quantities are expressed as % by weight based on the total weight of the composition.

Method

1-{[3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide (10 mg±1 mg) is weighed into a scintillation vial and 5 mL of the appropriate vehicle is added using a Gilson Pipette. Each mixture is treated with ultrasonics for 2 minutes with occasional hand shaking to ensure complete dispersion and wetting. The samples are then placed on a mechanical shaker and gently agitated overnight.

Suspension

A suspension composition of 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide is prepared, for example, using the following excipients:—

| | |
|---|---|
| 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide | 0.2% |
| Xylitol | 4.5% |
| Potassium Sorbate | 0.3% |
| EDTA (Edetate disodium dihydrate) | 0.015% |
| Sodium Citrate | 1.48% |
| Citric Acid | 0.96% |
| Polysorbate 80 | 0.005% |
| Water | to 100% |

Solution

A solution composition of 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide is prepared, for example, using the following excipients:—

| | |
|---|---|
| 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide | 0.2% |
| Xylitol | 4.5% |
| Potassium Sorbate | 0.3% |
| EDTA (Edetate disodium dihydrate) | 0.015% |
| Sodium Citrate | 1.48% |
| Citric Acid | 0.96% |

| Polysorbate 80 | 1.0% |
| Water | to 100% |

Biological Experimental
In Vitro Data
Glucocorticoid Receptor Binding Assay

The ability of compounds to bind to the glucocorticoid receptor was determined by assessing their ability to compete with an Alexa 555 fluorescently-labelled dexamethasone derivative. Compounds were solvated and diluted in DMSO, and transferred directly into assay plates. Fluorescent dexamethasone and a partially purified full length glucocorticoid receptor were added to the plates, together with buffer components to stabilise the GR protein (including stabilisation peptide (Panvera catalogue number P2815)) and incubated at room temperature for 2 hours in the dark. Binding of each compound was assessed by analysing the displacement of fluorescent ligand by measuring the decrease in fluorescence polarisation signal from the mixture.

Examples 1, 1-A, 1-B, 2, 2-A, 2-B, 3, 3-A, 3-B, 4, 5, 5-A, 5-B, 6, 7, 7-A, 7-B and 8 to 15 show glucocorticoid binding with a $pIC_{50}>7$ in this assay.

Glucocorticoid Mediated Transrepression of NFkB Activity

Human A549 lung epithelial cells were engineered to contain a secreted placental alkaline phosphatase gene under the control of the distal region of the NFkB dependent ELAM promoter as previously described in Ray, K. P., Farrow, S., Daly, M., Talabot, F. and Searle, N. "Induction of the E-selectin promoter by interleukin 1 and tumour necrosis factor alpha, and inhibition by glucocorticoids" *Biochemical Journal* (1997) 328: 707-15.

Compounds were solvated and diluted in DMSO, and transferred directly into assay plates such that the final concentration of DMSO was 0.7%. Following the addition of cells (40K per well), plates were incubated for 1 hr prior to the addition of 3 ng/ml human recombinant TNFα. Following continued incubation for 16 hr, alkaline phosphatase activity was determined by measuring the change in optical density at 405 nM with time following the addition of 0.7 volumes of assay buffer (1 mg/ml p-nitrophenylphosphate dissolved in 1M diethanolamine, 0.28M NaCl, 0.5 mM $MgCl_2$). Dose response curves were constructed from which $EC_{50}$ values were estimated.

Examples 1, 1-A, 2, 2-A, 2-B, 3, 3-A, 4, 5, 5-A, 6, 7, 7-A and 8 to 17 show $pEC_{50}>8.5$ in this assay.

Assay for Progesterone Receptor Activity

A T225 flask of CV-1 cells at a density of 80% confluency was washed with PBS, detached from the flask using 0.25% trypsin and counted using a Sysmex KX-21N. Cells were diluted in DMEM containing 10% Hyclone, 2 mM L-Glutamate and 1% Pen/Strep at 140 cells/μl and transduced with 10% PRb-BacMam and 10% MMTV-BacMam. 70 ml of suspension cells were dispensed to each well of white Nunc 384-well plates, containing compounds at the required concentration. After 24 h 10 μl of Steadylite were added to each well of the plates. Plates were incubated in the dark for 10 min before reading them on a Viewlux reader. Dose response curves were constructed from which $pEC_{50}$ values were estimated.

Examples 1-B, 2, 2-A, 2-B, 3-B, 5-B, 6, 7, 7-A, 7-B, 8 to 10, 12, 14 to 17 show $pEC_{50}<8$ in this assay.

In describing examples according to their activity in the assays above, it will be appreciated that at least one isomer, for example, an enantiomer in a mixture of isomers (such as a racemate) has the described activity. The other enantiomer may have similar activity, less activity, no activity or may have some antagonist activity in the case of a functional assay.

In Vivo Data
Intra Nasally Dosed LPS Induced Neutrophilia in the Male CD Rat
Compound/Vehicle Pretreatment Male CD rats 150-200 g were anaesthetised with isoflurane (5%, 2 L/min $O_2$, 1 L/min NO) and held vertically whilst being dosed with test compound or vehicle (0.2% Tween 80 in saline) at a dose volume of 25 μl per nostril, using a 100 μp Gilson pipette. The tip of the pipette was inserted approximately 3 mm into the nostril and the dosing substance instilled. After dosing, animals were placed in a supine position during recovery from anaesthesia.

LPS Challenge Protocol

Approximately thirty minutes following dosing of compound or vehicle the rats were re-anaesthetised as above then dosed in the same manner with 25 μl/nostril of either phosphate buffered saline vehicle, (PBS) or 10 mg/ml lipopolysaccharide (LPS).

Nasal Lavage Protocol

Four hours following the PBS/LPS challenge the animals were culled with an overdose of sodium pentobarbitone given intra peritoneally. The trachea was exposed and a small incision made, into which a tube was inserted orthograde towards the nasal cavity. The nose was then washed with 15 mls of nasal lavage (NAL) fluid (3.72 g EDTA and 1 g bovine serum albumin, dissolved in 1 liter of PBS).

NAL samples were centrifuged at 1300 rpm for 7 minutes, the resulting cell pellet was re-suspended in 0.5 ml NAL fluid, and 100 μp was subjected to FACS analysis to determine neutrophil count. Neutrophils were expressed per ml of the original NAL volume.

Oxazolone Induced Mouse Ear Skin Delayed Type Hypersensitivity Model (DTH)
Sensitisation Protocol Prior to sensitisation the flanks of all mice (female BALB/c 10-14 g, Charles River, UK) were shaved to allow better contact of the sensitising agent with the skin. Vehicle only (1 part Olive oil to 4 parts Acetone) was applied to a background group. Sensitisation was by topical application of 50 μl of a 2.5% Oxazolone solution (25 mg/ml) on to the shaved flank. Five days later ear thickness was measured under anaesthesia (5% Isoflurane, 2 L/min $O_2$) using engineers callipers.

Compound Dosing Protocol

One hour prior to, and three hours post challenge, animals were dosed topically, under anaesthesia on the right ear only with 10 μl vehicle (ethanol) or compound solution.

Challenge Protocol

Animals were challenged, under anaesthesia with 0.25% oxazolone solution (2.5 mg/ml in 1 part Olive oil to 4 parts Acetone; 20 μl on the dorsum of each ear). Twenty four hours after challenge the ear thickness was re-measured.

The mean ear thickness of the background group was then subtracted from the challenge and compound treated groups to give the specific increase in ear thickness induced by each treatment. The untreated left ear gives an indication of systemic activity of the test compounds.

In the in vivo model systems tested, 1-{[3-(4-{[(2R)-4-[5-fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide was found to be of similar or greater potency than fluticasone propionate.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The patents and patent applications described in this application are herein incorporated by reference.

The inventionn cliamed is:

1. 1-{[3-(4-{[(2R)-4-[5-Fluoro-2-(methyloxy)phenyl]-2-hydroxy-4-methyl-2-(trifluoromethyl)pentyl]amino}-6-methyl-1H-indazol-1-yl)phenyl]carbonyl}-D-prolinamide:

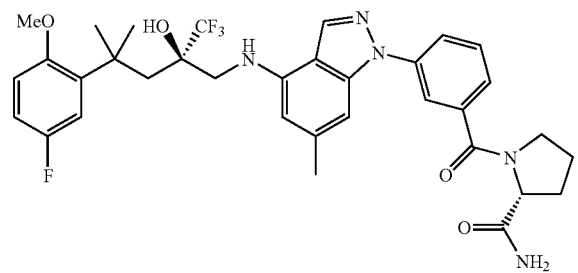

2. A pharmaceutical composition comprising a compound as claimed in claim 1, optionally in admixture with one or more physiologically acceptable diluents or carriers.

3. A pharmaceutical composition according to claim 2, wherein said composition is adapted for intranasal delivery.

4. A pharmaceutical composition comprising the compound of claim 1, in combination with one or more therapeutically active agents.

5. 1-{[3-(4-{[(2R)-4-[5-Fluoro-2-(methyloxy) phenyl]-2-hydroxy-4-methyl-2-(trifluoromethyl)pentyl]amino}-6-methyl-1H-indazol-1-yl) phenyl]carbonyl}-D-prolinamide:

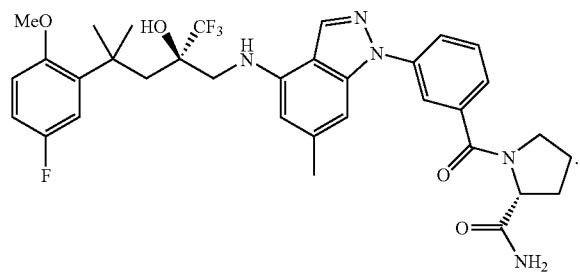

or a salt thereof.

6. A pharmaceutical composition comprising 1-{[3-(4-{[(2R)-4-[5-Fluoro-2-(methyloxy) phenyl]-2-hydroxy-4-methyl-2-(trifluoromethyl)pentyl]amino}-6-methyl-1H-indazol-1-yl)phenyl]carbonyl}-D-prolinamide:

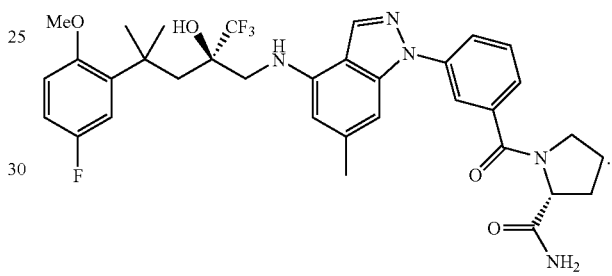

and one or more suspending agents.

* * * * *